United States Patent
Flasinski

(10) Patent No.: US 11,499,159 B2
(45) Date of Patent: Nov. 15, 2022

(54) PLANT REGULATORY ELEMENTS AND USES THEREOF

(71) Applicant: Monsanto Technology LLC, St. Louis, MO (US)

(72) Inventor: Stanislaw Flasinski, Ballwin, MO (US)

(73) Assignee: MONSANTO TECHNOLOGY LLC, St. Louis, MO (US)

(*) Notice: Subject to any disclaimer, the term of this patent is extended or adjusted under 35 U.S.C. 154(b) by 0 days.

(21) Appl. No.: 16/738,313

(22) Filed: Jan. 9, 2020

(65) Prior Publication Data

US 2020/0224213 A1 Jul. 16, 2020

Related U.S. Application Data

(60) Provisional application No. 62/790,570, filed on Jan. 10, 2019.

(51) Int. Cl.
*C12N 15/82* (2006.01)

(52) U.S. Cl.
CPC ..... *C12N 15/8216* (2013.01); *C12N 15/8218* (2013.01); *C12N 15/8225* (2013.01); *C12N 15/8227* (2013.01); *C12N 15/8274* (2013.01); *C12N 15/8279* (2013.01)

(58) Field of Classification Search
None
See application file for complete search history.

(56) References Cited

U.S. PATENT DOCUMENTS

| 6,211,431 B1 | 4/2001 | Boevink et al. |
| 7,193,133 B2 | 3/2007 | Lassner et al. |
| 9,637,736 B2 | 5/2017 | Flasinki et al. |
| 2014/0283200 A1* | 9/2014 | Chittoor ............. C12N 15/8216 800/278 |

FOREIGN PATENT DOCUMENTS

| IN | 580/KOL/2014 | * | 8/2016 |
| WO | 2015181823 A1 | | 12/2015 |

OTHER PUBLICATIONS

Riethoven. Regulatory regions in DNA: promoters, enhancers, silencers, and insulators. Methods Mol. Biol. 2010;674:33-42. (Year: 2010).*
Weiher et al. Multiple point mutations affecting the simian virus 40 enhancer. Science. Feb. 11, 1983;219(4585):626-31. (Year: 1983).*
Davies et al. Identification and use of the sugarcane bacilliform virus enhancer in transgenic maize. BMC Plant Biol. Dec. 19, 2014; 14:359. (Year: 2014).*
International Search Report and Written Opinion regarding International Application No. PCT/US2020/012872 dated Jun. 2, 2020.
GenBank Accession No. CA284593.1, accessed on Apr. 28, 2020.
Invitation to Pay Additional Fees regarding International Application No. PCT/US2020/012872 dated Mar. 17, 2020.
Mayr, et al., "Regulation by 3'-Untranslated Regions," Annual Review of Genetics, 2017, 171-194, 51.
Xie, et. al., "Systematic discovery of regulatory motifs in human promoters and 3' UTRs by comparison of several mammals," Nature, 2005, 338-345, 434.
Barret, et. al., "Regulation of eukaryotic gene expression by the untranslated regions and other non-coding elements," Cell. Mol. Life Sci., 2012, 3613-3634, 69.
Extended European Search Report regarding European App. No. 20738534.5, dated Aug. 22, 2022.
Li et al., A MITE insertion into the 3'-UTR regulates the transcription of TAHSP16.9 in common wheat, The Crop Journal 2(6):381-387, 2014.
Rosenthal et al., An intronless form of the tobacco extensin gene terminator strongly enhances transient gene expression in plant leaves, Plant Molecular Biology 96(4): 429-443, 2018.
Srivastava et al., UTR-dependent control of gene expression in plants, Trends in Plant Science 23(3): 248-259, 2018.

* cited by examiner

*Primary Examiner* — Cynthia E Collins
(74) *Attorney, Agent, or Firm* — Dentons US LLP; Judith Koehler, Esq.

(57) ABSTRACT

The invention provides recombinant DNA molecules and constructs, as well as their nucleotide sequences, useful for modulating gene expression in plants. The invention also provides transgenic plants, plant cells, plant parts, and seeds comprising the recombinant DNA molecules operably linked to heterologous transcribable DNA molecules, as are methods of their use.

17 Claims, No Drawings
Specification includes a Sequence Listing.

PLANT REGULATORY ELEMENTS AND USES THEREOF

REFERENCE TO RELATED APPLICATION

This application claims the benefit of U.S. provisional application No. 62/790,570, filed Jan. 10, 2019, which is herein incorporated by reference in its entirety.

INCORPORATION OF SEQUENCE LISTING

The sequence listing that is contained in the file named "MONS468US_ST25.txt", is 33,896 bytes (as measured in Microsoft Windows®), was created on Jan. 9, 2020, and is filed herewith by electronic submission and incorporated by reference herein.

FIELD OF THE INVENTION

The invention relates to the field of plant molecular biology and plant genetic engineering. More specifically, the invention relates to DNA molecules useful for modulating gene expression in plants.

BACKGROUND

Regulatory elements are genetic elements that regulate gene activity by modulating the transcription of an operably linked transcribable DNA molecule. Such elements may include promoters, leaders, introns, and 3' untranslated regions and are useful in the field of plant molecular biology and plant genetic engineering.

SUMMARY OF THE INVENTION

The invention provides novel gene regulatory elements for use in plants. The invention also provides recombinant DNA molecules constructs comprising the regulatory elements. The present invention also provides transgenic plant cells, plants, and seeds comprising the regulatory elements. In one embodiment, the regulatory elements are operably linked to a transcribable DNA molecule. In certain embodiments, the transcribable DNA molecule may be heterologous with respect to the regulatory sequence. Thus, a regulatory element sequence provided by the invention may, in particular embodiments, be defined as operably linked to a heterologous transcribable DNA molecule. The present invention also provides methods of using the regulatory elements and making and using the recombinant DNA molecules comprising the regulatory elements, and the transgenic plant cells, plants, and seeds comprising the regulatory elements operably linked to a transcribable DNA molecule.

Thus, in one aspect, the invention provides a recombinant DNA molecule comprising a DNA sequence selected from the group consisting of: (a) a sequence with at least about 85 percent sequence identity to any of SEQ ID NOs:2-8, 12-14, and 16-19; (b) a sequence comprising any of SEQ ID NOs:2-8, 12-14, and 16-19; and (c) a fragment of any of SEQ ID NOs:2-8, 12-14, and 16-19, wherein the fragment has gene-regulatory activity; wherein the sequence is operably linked to a heterologous transcribable DNA molecule. By "heterologous transcribable DNA molecule," it is meant that the transcribable DNA molecule is heterologous with respect to the polynucleotide sequence to which it is operably linked. In specific embodiments, the recombinant DNA molecule comprises a DNA sequence having at least about 85 percent, at least about 86 percent, at least about 87 percent, at least about 88 percent, at least about 89 percent, at least about 90 percent, at least 91 percent, at least 92 percent, at least 93 percent, at least 94 percent, at least 95 percent, at least 96 percent, at least 97 percent, at least 98 percent, or at least 99 percent sequence identity to the DNA sequence of any of SEQ ID NOs:2-8, 12-14, and 16-19. In particular embodiments, the DNA sequence comprises a regulatory element. In some embodiments, the regulatory element comprises a promoter operably linked to an intron. In still other embodiments, the regulatory element comprises a 3' UTR. In still other embodiments, the heterologous transcribable DNA molecule comprises a gene of agronomic interest, such as a gene capable of providing herbicide resistance in plants, or a gene capable of providing plant pest resistance in plants. In still other embodiments, the heterologous transcribable DNA molecule comprises a sequence encoding a small RNA, such as a dsRNA, an miRNA, or siRNA. In still other embodiments, the invention provides a construct comprising a recombinant DNA molecule as provided herein.

In another aspect, provided herein are transgenic plant cells comprising a recombinant DNA molecule comprising a DNA sequence selected from the group consisting of: (a) a sequence with at least about 85 percent sequence identity to any of SEQ ID NOs:2-8, 12-14, and 16-19; (b) a sequence comprising any of SEQ ID NOs:2-8, 12-14, and 16-19; and (c) a fragment of any of SEQ ID NOs:2-8, 12-14, and 16-19, wherein the fragment has gene-regulatory activity; wherein the DNA sequence is operably linked to a heterologous transcribable DNA molecule. In certain embodiments, the transgenic plant cell is a monocotyledonous plant cell. In other embodiments, the transgenic plant cell is a monocotyledonous plant cell or a dicotyledonous plant cell.

In still yet another aspect, further provided herein is a transgenic plant, or part thereof, comprising a recombinant DNA molecule comprising a DNA sequence selected from the group consisting of: a) a sequence with at least 85 percent sequence identity to any of SEQ ID NOs:2-8, 12-14, and 16-19; b) a sequence comprising any of SEQ ID NOs:2-8, 12-14, and 16-19; and c) a fragment of any of SEQ ID NOs:2-8, 12-14, and 16-19, wherein the fragment has gene-regulatory activity; wherein the sequence is operably linked to a heterologous transcribable DNA molecule. In specific embodiments, the transgenic plant is a progeny plant of any generation that comprises the recombinant DNA molecule. A transgenic seed comprising the recombinant DNA molecule that produces such a transgenic plant when grown is also provided herein.

In another aspect, the invention provides a method of producing a commodity product comprising obtaining a transgenic plant or part thereof containing a recombinant DNA molecule of the invention and producing the commodity product therefrom. In one embodiment, the commodity product is seeds, processed seeds, protein concentrate, protein isolate, starch, grains, plant parts, seed oil, biomass, flour and meal.

In still yet another aspect, the invention provides a method of producing a transgenic plant comprising a recombinant DNA molecule of the invention comprising transforming a plant cell with the recombinant DNA molecule of the invention to produce a transformed plant cell and regenerating a transgenic plant from the transformed plant cell.

BRIEF DESCRIPTION OF THE SEQUENCES

SEQ ID NO:1 is a DNA sequence of the 3' UTR, T-SETit.Ams1:1, derived from the S-adenosylmethionine synthetase 1 protein gene from *Setaria italica* (Foxtail millet).

SEQ ID NO:2 is a DNA sequence of the 3' UTR, T-Cl.Hsp16.9_2:1, derived from the Hsp16.9 (heat shock protein 16.9) protein gene from *Coix lacryma-jobi* (Job's tears).

SEQ ID NO:3 is a DNA sequence of the 3' UTR, T-ERIra.Hsp17.9_3:1, derived from a putative heat shock protein gene from *Eragrostis tef* (Tef).

SEQ ID NO:4 is a DNA sequence of the 3' UTR, T-ERIra.Hsp16.9_3:1, derived from the Hsp16.9 (Heat shock protein 16.9) protein gene from *Saccharum ravennae* (hardy pampas grass).

SEQ ID NO:5 is a DNA sequence of the 3' UTR, T-ANDge.Hsp/Sb.Hsp, a chimeric 3' UTR derived from heat shock protein genes from *Andropogon gerardii* (big bluestem) and Sorghum bicolor (Sorghum).

SEQ ID NO:6 is a DNA sequence of an EXP, EXP-Zm.LTP-SETit.Act4 comprising a promoter and 5' UTR derived from a lipid transfer protein-like protein gene from *Zea mays*, operably linked 5' to an intron derived from an actin 4 gene from *Setaria italica*.

SEQ ID NO:7 is a DNA sequence of a promoter, P-Zm.Ltp-1:1:2, derived from a lipid transfer protein-like protein from *Zea mays*.

SEQ ID NO:8 is a DNA sequence of a 5' UTR (leader), L-Zm.Ltp-1:1:3, derived from a lipid transfer protein-like protein from *Zea mays*.

SEQ ID NO:9 is a DNA sequence of an intron, I-SETit.Act4:2, derived from an actin 4 gene from *Setaria italica*.

SEQ ID NO:10 is a DNA sequence of an enhancer, E-CaMV.35S-RC derived from the Cauliflower mosaic virus 35S promoter in a reverse compliment orientation.

SEQ ID NO:11 is a synthetic coding sequence optimized for plant expression for β-glucuronidase (GUS) with a processable intron derived from the potato light-inducible tissue-specific ST-LS1 gene (GenBank Accession: X04753).

SEQ ID NO:12 is a DNA sequence of the 3' UTR, T-Cl.Hsp16.9:2, derived from the Hsp16.9 (Heat shock protein 16.9) protein gene from *Saccharum ravennae* (hardy pampas grass).

SEQ ID NO:13 is a DNA sequence of the 3' UTR, T-Cl.Hsp16.9:2, derived from the Hsp16.9 (heat shock protein 16.9) protein gene from *Coix lacryma-jobi* (Job's tears).

SEQ ID NO:14 is a DNA sequence of a chimeric-rearranged enhancer, E-DaMV.H-Flt:1, derived from multiple public Dahlia mosaic virus promoters. A first fragment is derived from the promoter of the DaMV-Holland (DaMV-H) strain, Genbank accession EU090957, nucleotides 1177-1494. This fragment is operably linked to a second fragment derived from the DaMV-H promoter, nucleotides 1003-1176. In the native DaMV promoter configuration, the second fragment would precede the first fragment. Within the first fragment, nucleotides 287 through 288, and nucleotides 319 through 322 were changed to sequences in analogous locations of a DaMV promoter within Genbank accession JX272320.

SEQ ID NO:15 is a DNA sequence of an enhancer, E-DaMV.FLT:2, derived from a Dalia mosaic virus promoter, Genbank accession EF513491, nucleotides 1 through 322.

SEQ ID NO:16 is a DNA sequence of an EXP, EXP-DaMV.H-Flt+Zm.Ltp+SETit.Act4:1 comprised of the chimeric-rearranged enhancer, E-DaMV.H-Flt:1 (SEQ ID NO:14), operably linked 5' to the promoter and 5' UTR derived from a lipid transfer protein-like protein gene from *Zea mays*, operably linked 5' to an intron derived from an actin 4 gene from *Setaria italica*.

SEQ ID NO:17 is a DNA sequence of an EXP, EXP-DaMV.H-Flt+Zm.Ltp+SETit.Act4:1 comprised of the chimeric-rearranged enhancer, E-DaMV.H-Flt:1 (SEQ ID NO:14), operably linked 5' to the promoter and 5' UTR derived from a lipid transfer protein-like protein gene from *Zea mays*, operably linked 5' to an intron derived from an actin 4 gene from *Setaria italica*. The chimeric-rearranged E-DaMV.H-Flt:1 enhancer is cloned in the opposite orientation relative to EXP-DaMV.H-Flt+Zm.Ltp+SETit.Act4:1 (SEQ ID NO:16).

SEQ ID NO:18 is a DNA sequence of an EXP, EXP-DaMV.FLT+Td.RCc3_1+SETit.14-3-3C-5:1 comprised of the enhancer, E-DaMV.FLT:2 operably linked 5' to the promoter and 5' UTR derived from an RCc3 gene from *Trypsicum dactyloides*, operably linked 5' to an intron derived from a 14-3-3C gene from *Setaria italica*.

SEQ ID NO:19 is a DNA sequence of an EXP, EXP-DaMV.FLT+Td.RCc3_1+SETit.14-3-3C-5:1 comprised of the enhancer, E-DaMV.FLT:2 operably linked 5' to the promoter and 5' UTR derived from an RCc3 gene from *Trypsicum dactyloides*, operably linked 5' to an intron derived from a 14-3-3C gene from *Setaria italica*. The E-DaMV.FLT:2 enhancer is cloned in the opposite orientation relative to EXP-DaMV.FLT+Td.RCc3_1+SETit.14-3-3C-5:1 (SEQ ID NO:18).

DETAILED DESCRIPTION OF THE INVENTION

The invention provides regulatory elements having gene-regulatory activity in plants. The nucleotide sequences of these regulatory elements are provided as SEQ ID NOs:2-8, 12-14, and 16-19. These regulatory elements are capable of affecting the expression of an operably linked transcribable DNA molecule in plant tissues, and therefore regulating gene expression of an operably linked transgene in transgenic plants. The invention also provides methods of modifying, producing, and using recombinant DNA molecules which contain the provided regulatory elements. The invention also provides compositions that include transgenic plant cells, plants, plant parts, and seeds containing the recombinant DNA molecules of the invention, and methods for preparing and using the same.

The following definitions and methods are provided to better define the present invention and to guide those of ordinary skill in the art in the practice of the present invention. Unless otherwise noted, terms are to be understood according to conventional usage by those of ordinary skill in the relevant art.

DNA Molecules

As used herein, the term "DNA" or "DNA molecule" refers to a double-stranded DNA molecule of genomic or synthetic origin, i.e., a polymer of deoxyribonucleotide bases or a DNA molecule, read from the 5' (upstream) end to the 3' (downstream) end. As used herein, the term "DNA sequence" refers to the nucleotide sequence of a DNA molecule. The nomenclature used herein corresponds to that of Title 37 of the United States Code of Federal Regulations § 1.822, and set forth in the tables in WIPO Standard ST.25 (1998), Appendix 2, Tables 1 and 3.

As used herein, a "recombinant DNA molecule" is a DNA molecule comprising a combination of DNA molecules that would not naturally occur together without human intervention. For instance, a recombinant DNA molecule may be a DNA molecule that is comprised of at least two DNA molecules heterologous with respect to each other, a DNA molecule that comprises a DNA sequence that deviates from DNA sequences that exist in nature, a DNA molecule that comprises a synthetic DNA sequence or a DNA molecule that has been incorporated into a host cell's DNA by genetic transformation or gene editing.

Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

As used herein, the term "sequence identity" refers to the extent to which two optimally aligned polynucleotide sequences or two optimally aligned polypeptide sequences are identical. An optimal sequence alignment is created by manually aligning two sequences, e.g., a reference sequence and another sequence, to maximize the number of nucleotide matches in the sequence alignment with appropriate internal nucleotide insertions, deletions, or gaps. As used herein, the term "reference sequence" refers to a DNA sequence provided as SEQ ID NOs:2-8, 12-14, and 16-19.

As used herein, the term "percent sequence identity" or "percent identity" or "% identity" is the identity fraction multiplied by 100. The "identity fraction" for a sequence optimally aligned with a reference sequence is the number of nucleotide matches in the optimal alignment, divided by the total number of nucleotides in the reference sequence, e.g., the total number of nucleotides in the full length of the entire reference sequence. Thus, one embodiment of the invention provides a DNA molecule comprising a sequence that, when optimally aligned to a reference sequence, provided herein as SEQ ID NOs:2-8, 12-14, and 16-19, has at least about 85 percent identity, at least about 86 percent identity, at least about 87 percent identity, at least about 88 percent identity, at least about 89 percent identity, at least about 90 percent identity, at least about 91 percent identity, at least about 92 percent identity, at least about 93 percent identity, at least about 94 percent identity, at least about 95 percent identity, at least about 96 percent identity, at least about 97 percent identity, at least about 98 percent identity, at least about 99 percent identity, or at least about 100 percent identity to the reference sequence. DNA molecules having a percent sequence identity with reference molecule may exhibit the activity of the reference sequence.

Regulatory Elements

Regulatory elements such as promoters, leaders (also known as 5' UTRs), enhancers, introns, and transcription termination regions (or 3' UTRs) play an integral part in the overall expression of genes in living cells. The term "regulatory element," as used herein, refers to a DNA molecule having gene-regulatory activity. The term "gene-regulatory activity," as used herein, refers to the ability to affect the expression of an operably linked transcribable DNA molecule, for instance by affecting the transcription and/or translation of the operably linked transcribable DNA molecule. Regulatory elements, such as promoters, leaders, enhancers, introns and 3' UTRs that function in plants are useful for modifying plant phenotypes through genetic engineering.

As used herein, a "regulatory expression element group" or "EXP" sequence may refer to a group of operably linked regulatory elements, such as enhancers, promoters, leaders, and introns. For example, a regulatory expression element group may be comprised, for instance, of a promoter operably linked 5' to a leader sequence, operably linked 5' to an intron sequence. An EXP useful in practicing the present invention is presented as SEQ ID NOs:6, 16, 17, 18, and 19.

Regulatory elements may be characterized by their gene expression pattern, e.g., positive and/or negative effects such as constitutive expression or temporal, spatial, developmental, tissue, environmental, physiological, pathological, cell cycle, and/or chemically responsive expression, and any combination thereof, as well as by quantitative or qualitative indications. As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a double-stranded RNA (dsRNA), a transfer RNA (tRNA), a ribosomal RNA (rRNA), a microRNA (miRNA), a small interfering RNA (siRNA), and the like.

As used herein, the term "protein expression" is any pattern of translation of a transcribed RNA molecule into a protein molecule. Protein expression may be characterized by its temporal, spatial, developmental, or morphological qualities, as well as by quantitative or qualitative indications.

A promoter is useful as a regulatory element for modulating the expression of an operably linked transcribable DNA molecule. As used herein, the term "promoter" refers generally to a DNA molecule that is involved in recognition and binding of RNA polymerase II and other proteins, such as trans-acting transcription factors, to initiate transcription. A promoter may be initially isolated from the 5' untranslated region (5' UTR) of a genomic copy of a gene. Alternately, promoters may be synthetically produced or manipulated DNA molecules. Promoters may also be chimeric. Chimeric promoters are produced through the fusion of two or more heterologous DNA molecules. A promoter useful in practicing the present invention is provided as SEQ ID NO:7, or the promoter comprised within SEQ ID NO:18, or a fragment or variant thereof. In specific embodiments of the invention, the claimed DNA molecules and any variants or derivatives thereof as described herein, are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" which provides a basal level of transcription and is comprised of a TATA box or equivalent DNA sequence for recognition and binding of the RNA polymerase II complex for initiation of transcription.

In one embodiment, fragments of an EXP sequence or a promoter sequence disclosed herein are provided. Promoter fragments may comprise promoter activity, as described above, and may be useful alone or in combination with other promoters and promoter fragments, such as in constructing chimeric promoters, or in combination with other expression elements and expression element fragments. In specific embodiments, fragments of a promoter are provided comprising at least about 50, at least about 75, at least about 95, at least about 100, at least about 125, at least about 150, at least about 175, at least about 200, at least about 225, at least about 250, at least about 275, at least about 300, at least about 350, at least about 400, at least about 450, at least about 500, at least about 550, at least about 600, at least about 650, at least about 700, at least about 750, at least about 800, at least about 900, at least about 1000, at least about 1100, at least about 1200, at least about 1300, at least about 1400, at least about 1500, at least about 1600, at least about 1700, at least about 1800, at least about 1900, or at least about 2000 contiguous nucleotides, or longer, of a DNA molecule having promoter activity as disclosed herein. Methods for producing such fragments from a starting promoter molecule are well known in the art.

Compositions derived from the promoter provided in SEQ ID NO:7, or the promoter comprised within SEQ ID NO:18, such as internal or 5' deletions, for example, can be produced using methods known in the art to improve or alter expression, including by removing elements that have either positive or negative effects on expression; duplicating elements that have positive or negative effects on expression; and/or duplicating or removing elements that have tissue- or cell-specific effects on expression. Compositions derived from the promoter provided in SEQ ID NO:7, or the promoter comprised within SEQ ID NO:18, comprised of 3' deletions in which the TATA box element or equivalent sequence thereof and downstream sequence is removed can be used, for example, to make enhancer elements. Further deletions can be made to remove any elements that have positive or negative; tissue-specific; cell-specific; or timing-specific (such as, but not limited to, circadian rhythm) effects on expression. The promoter element provided in SEQ ID NO:7 or the promoter comprised within SEQ ID NO:18, and fragments or enhancers derived therefrom can be used to make chimeric transcriptional regulatory element compositions.

In accordance with the invention, a promoter or promoter fragment may be analyzed for the presence of known promoter elements, i.e., DNA sequence characteristics, such as a TATA box and other known transcription factor binding site motifs. Identification of such known promoter elements may be used by one of skill in the art to design variants of the promoter having a similar expression pattern to the original promoter.

As used herein, the term "leader" refers to a DNA molecule isolated from the untranslated 5' region (5' UTR) a gene and defined generally as a nucleotide segment between the transcription start site (TSS) and the protein coding sequence start site. Alternately, leaders may be synthetically produced or manipulated DNA elements. A leader can be used as a 5' regulatory element for modulating expression of an operably linked transcribable DNA molecule. Leader molecules may be used with a heterologous promoter or with their native promoter. A leader useful in practicing the present invention is provided as SEQ ID NO:8 and the leader comprised within SEQ ID NO:18. In specific embodiments, such DNA sequences may be defined as being capable of acting as a leader in a host cell, including, for example, a transgenic plant cell. In one embodiment, such sequences are decoded as comprising leader activity.

The leader sequences (also referred to as 5' UTRs) presented as SEQ ID NO:8, or the leader comprised within SEQ ID NO:18, may be comprised of regulatory elements, or may adopt secondary structures that can have an effect on transcription or translation of an operably linked transcribable DNA molecule. The leader sequences presented as SEQ ID NOs:8, or the leader comprised within SEQ ID NO:18, can be used in accordance with the invention to make chimeric regulatory elements that affect transcription or translation of a an operably linked transcribable DNA molecule.

As used herein, the term "intron" refers to a DNA molecule that may be isolated or identified from a gene and may be defined generally as a region spliced out during messenger RNA (mRNA) processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable DNA molecule. A construct may comprise an intron, and the intron may or may not be heterologous with respect to the transcribable DNA molecule. Examples of introns in the art include the rice actin intron and the corn HSP70 intron.

In plants, the inclusion of some introns in gene constructs leads to increased mRNA and protein accumulation relative to constructs lacking the intron. This effect has been termed "intron mediated enhancement" (IME) of gene expression. Introns known to stimulate expression in plants have been identified in maize genes (e.g., tubA1, Adh1, Sh1, and Ubi1), in rice genes (e.g., tpi) and in dicotyledonous plant genes like those from petunia (e.g., rbcS), potato (e.g., st-1s1) and from *Arabidopsis thaliana* (e.g., ubq3 and pat1). It has been shown that deletions or mutations within the splice sites of an intron reduce gene expression, indicating that splicing might be needed for IME. However, IME in dicotyledonous plants has been shown by point mutations within the splice sites of the pat1 gene from *A. thaliana*. Multiple uses of the same intron in one plant has been shown to exhibit disadvantages. In those cases, it is necessary to have a collection of basic control elements for the construction of appropriate recombinant DNA elements. Exemplary introns useful in practicing the present invention are presented as SEQ ID NOs:9 and the leader comprised within SEQ ID NO:18.

In one embodiment, fragments of an intron sequence disclosed herein are provided. Intron fragments may comprise intron activity, as described above, and may be useful alone or in combination with other expression elements and expression element fragments. In specific embodiments, fragments of an intron are provided comprising at least about 50, at least about 75, at least about 95, at least about 100, at least about 125, at least about 150, at least about 175, at least about 200, at least about 225, at least about 250, at least about 275, at least about 300, at least about 350, at least about 400, at least about 450, at least about 500, at least about 550, at least about 600, at least about 650, at least about 700, at least about 750, at least about 800, at least about 900, at least about 1000, at least about 1100, at least about 1200, at least about 1300, at least about 1400, at least about 1500, at least about 1600, at least about 1700, at least about 1800, at least about 1900, or at least about 2000 contiguous nucleotides, or longer, of a DNA molecule having intron activity as disclosed herein. Methods for producing such fragments from a starting intron molecule are well known in the art.

As used herein, the terms "3' transcription termination molecule," "3' untranslated region" or "3' UTR" refer to a DNA molecule that is used during transcription to the untranslated region of the 3' portion of an mRNA molecule. The 3' untranslated region of an mRNA molecule may be generated by specific cleavage and 3' polyadenylation, also known as a polyA tail. A 3' UTR may be operably linked to and located downstream of a transcribable DNA molecule and may include a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region, wheat hsp17 3' region, pea rubisco small subunit 3' region, cotton E6 3' region, and the coixin 3' UTR.

3' UTRs typically find beneficial use for the recombinant expression of specific DNA molecules. A weak 3' UTR has the potential to generate read-through, which may affect the expression of the DNA molecule located in the neighboring expression cassettes. Appropriate control of transcription termination can prevent read-through into DNA sequences (e.g., other expression cassettes) localized downstream and can further allow efficient recycling of RNA polymerase to improve gene expression. Efficient termination of transcription (release of RNA Polymerase II from the DNA) is prerequisite for re-initiation of transcription and thereby directly affects the overall transcript level. Subsequent to transcription termination, the mature mRNA is released from the site of synthesis and template transported to the cytoplasm. Eukaryotic mRNAs are accumulated as poly(A) forms in vivo, making it difficult to detect transcriptional termination sites by conventional methods.

Regulation of gene function through 3' UTRs is a relatively new field as only recent sequencing technology has provided us with the full landscape of 3' UTRs across species and cell types. Before sequencing technology was available, detailed functional and mechanistic studies were performed only on a few model 3' UTRs. Although these model 3' UTRs have contributed substantially to our understanding of 3' UTR biology, the conclusions drawn about their regulatory functions have been limited and were focused more on mRNA stability. (Mayr, Christine (2017) *Regulation by 3'-Untranslated Regions*. Annual Review of Genetics, 51: 171-194) A genome-wide in silico analysis revealed that motifs in the 3' UTR are primarily conserved on one strand, which is consistent with the 3' UTR acting to regulate gene expression at the post-transcriptional level (Xie, X. et. al., (2005) *Systematic discovery of regulatory motifs in human promoters and 3' UTRs by comparison of several mammals*, Nature 434: 338-345). 3' UTRs determine protein levels through regulation of mRNA stability and translation mediated largely by AU-rich elements and miR-NAs. 3' UTRs also enable local translation through the regulation of mRNA localization. A 3' UTR's length can be regulated by alternative cleavage and polyadenylation. 3' UTRs mediate protein-protein interactions (PPIs) which has widespread consequences for protein complex formation, protein localization, and protein function. 3' UTRs regulate gene expression through the binding of RNA-binding proteins (RBPs). RBPs bind to 3' UTR cis-elements and mediate 3' UTR functions through the recruitment of effector proteins. RBPs cooperate with other bound RBPs to enable functional specificity in vivo. The composition of RBPs bound to a 3' UTR at a given moment is dynamic and can change depending on the local environment, e.g., through addition of posttranslational modifications, local expression of other RBPs, and interactions with membranes and cytoskeletal filaments. RBP binding is also influenced by secondary and tertiary RNA structure formation that regulates accessibility of 3' UTRs (Mayr, Christine (2017) *Regulation by 3'-Untranslated Regions*. Annual Review of Genetics, 51: 171-194).

The poly(A) tail results from the addition of a series of adenosine bases to the 3' end of an RNA molecule. This provides the mRNA with a binding site for a class of regulatory factors called the poly(A) binding proteins (PABP) that have roles in the regulation of gene expression, including mRNA export, stability and decay, and translation. The 5' cap structure of the mRNA and the poly-A tail function synergistically to control mRNA translation. The association of PABPs with the poly(A) tail facilitates an interaction with eIF4F bound to the 5' cap structure, resulting in circularisation of the mRNA that promotes translation initiation and ensures ribosome recycling and efficient translation. This interaction also allows inhibition of translation by inhibitor proteins bound to the 3' UTR (Barret, L et. al. (2012) *Regulation of eukaryotic gene expression by the untranslated regions and other non-coding elements*. Cell. Mol. Life Sci. 69:3613-3634).

From a practical standpoint, it is typically beneficial that a 3' UTR used in an expression cassette possesses the following characteristics. First, the 3' UTR should be able to efficiently and effectively terminate transcription of the transgene and prevent read-through of the transcript into any neighboring DNA sequence, which can be comprised of another expression cassette as in the case of multiple expression cassettes residing in one transfer DNA (T-DNA), or the neighboring chromosomal DNA into which the T-DNA has inserted. Second, the 3' UTR should not cause a reduction in the transcriptional activity imparted by the promoter, leader, enhancers, and introns that are used to drive expression of the DNA molecule, unless this is a desired outcome. Provided in the examples below is data that demonstrates using the same enhancer, promoter, leader and intron sequences to drive expression, the 3' UTRs presented as SEQ ID NOs:1-5 modulate expression differently from one another and demonstrate tissue-specific effects on protein expression. Finally, in plant biotechnology, the 3' UTR is often used for priming of amplification reactions of reverse transcribed RNA extracted from the transformed plant and used to: (1) assess the transcriptional activity or expression of the expression cassette once integrated into the plant chromosome; (2) assess the copy number of insertions within the plant DNA; and (3) assess zygosity of the resulting seed after breeding. The 3' UTR is also used in amplification reactions of DNA extracted from the transformed plant to characterize the intactness of the inserted cassette. 3' UTRs useful in practicing the present invention are presented as SEQ ID NOs:1-5 and 12-13.

In one embodiment, fragments of a 3' UTR sequence disclosed herein are provided. 3' UTR fragments may comprise 3' UTR activity, as described above, and may be useful alone or in combination with other expression elements and expression element fragments. In specific embodiments, fragments of a 3' UTR are provided comprising at least about 50, at least about 75, at least about 95, at least about 100, at least about 125, at least about 150, at least about 175, at least about 200, at least about 225, at least about 250, at least about 275, at least about 300, at least about 350, at least about 400, at least about 450, at least about 500, at least about 550, at least about 600, or at least about 650, or longer, of a DNA molecule having 3' UTR activity as disclosed herein. Methods for producing such fragments from a starting 3' UTR molecule are well known in the art.

As used herein, the term "enhancer" or "enhancer element" refers to a cis-acting regulatory element, a.k.a. cis-element, which confers an aspect of the overall expression pattern, but is usually insufficient alone to drive transcription, of an operably linked transcribable DNA molecule. Unlike promoters, enhancer elements do not usually include a transcription start site (TSS) or TATA box or equivalent DNA sequence. A promoter or promoter fragment may naturally comprise one or more enhancer elements that affect the transcription of an operably linked DNA sequence. An enhancer element may also be fused to a promoter to produce a chimeric promoter cis-element, which confers an aspect of the overall modulation of gene expression.

Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated polymerase chain reaction (PCR), and other conventional assays or by DNA sequence similarity analysis using known cis-element motifs or enhancer elements as a target sequence or target motif with conventional DNA sequence comparison methods, such as BLAST. The fine structure of an enhancer domain can be further studied by mutagenesis (or substitution) of one or more nucleotides or by other conventional methods known in the art. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable DNA molecules are encompassed by the invention. An enhancer useful in practicing the invention is provided as SEQ ID NO:10, 14, and 15.

In one embodiment, fragments of an enhancer sequence disclosed herein are provided. Enhancer fragments may comprise enhancer activity, as described above, and may be useful alone or in combination with other expression elements and expression element fragments. In specific embodiments, fragments of an enhancer are provided comprising at least about 50, at least about 75, at least about 95, at least about 100, at least about 125, at least about 150, at least about 175, at least about 200, at least about 225, at least about 250, at least about 275, at least about 300, at least about 350, at least about 400, or at least about 450, or longer, of a DNA molecule having enhancer activity as disclosed herein. Methods for producing such fragments from a starting enhancer molecule are well known in the art.

As used herein, the term "chimeric" refers to a single DNA molecule produced by fusing a first DNA molecule to a second DNA molecule, where neither the first nor the second DNA molecule would normally be found in that configuration, i.e. fused to the other. The chimeric DNA molecule is thus a new DNA molecule not otherwise normally found in nature. As used herein, the term "chimeric promoter" refers to a promoter produced through such manipulation of DNA molecules. A "chimeric enhancer" refers to an enhancer produced through manipulation of DNA molecules. A "chimeric intron" refers to an intron produced through manipulation of DNA molecules. A "chimeric 3' UTR" refers to a 3' UTR produced through manipulation of DNA molecules. A chimeric promoter, enhancer, intron, or 3' UTR may combine two or more DNA fragments, for example, the fusion of a promoter to an enhancer element. Thus, the design, construction, and use of chimeric promoters, enhancers, introns, or 3' UTRs according to the methods disclosed herein for modulating the expression of operably linked transcribable DNA molecules are encompassed by the present invention.

Chimeric regulatory elements can be designed to comprise various constituent elements which may be operatively linked by various methods known in the art, such as restriction enzyme digestion and ligation, ligation independent cloning, modular assembly of PCR products during amplification, or direct chemical synthesis of the regulatory element, as well as other methods known in the art. The resulting various chimeric regulatory elements can be comprised of the same, or variants of the same, constituent elements but differ in the DNA sequence or DNA sequences that comprise the linking DNA sequence or sequences that allow the constituent parts to be operatively linked. In the invention, the DNA sequences provided as SEQ ID NOs:2-8, 12-14, and 16-19 may provide regulatory element reference sequences, wherein the constituent elements that comprise the reference sequence may be joined by methods known in the art and may comprise substitutions, deletions, and/or insertions of one or more nucleotides or mutations that naturally occur in bacterial and plant cell transformation.

As used herein, the term "variant" refers to a second DNA molecule, such as a regulatory element, that is in composition similar, but not identical to, a first DNA molecule, and wherein the second DNA molecule still maintains the general functionality, i.e. the same or similar expression pattern, for instance through more or less equivalent transcriptional activity, of the first DNA molecule. A variant may be a shorter or truncated version of the first DNA molecule or an altered version of the sequence of the first DNA molecule, such as one with different restriction enzyme sites and/or internal deletions, substitutions, or insertions. A "variant" can also encompass a regulatory element having a nucleotide sequence comprising a substitution, deletion, or insertion of one or more nucleotides of a reference sequence, wherein the derivative regulatory element has more or less or equivalent transcriptional or translational activity than the corresponding parent regulatory molecule. Regulatory element "variants" will also encompass variants arising from mutations that naturally occur in bacterial and plant cell transformation. In the present invention, a polynucleotide sequence provided as SEQ ID NOs:2-8, 12-14, and 16-19 may be used to create variants that are similar in composition, but not identical to, the DNA sequence of the original regulatory element, while still maintaining the general functionality, i.e., the same or similar expression pattern, of the original regulatory element. Production of such variants of the invention is well within the ordinary skill of the art in light of the disclosure and is encompassed within the scope of the invention.

The efficacy of the modifications, duplications, or deletions described herein on the desired expression aspects of a particular transgene may be tested empirically in stable and transient plant assays, such as those described in the working examples herein, so as to validate the results, which may vary depending upon the changes made and the goal of the change in the starting DNA molecule.

Constructs

As used herein, the term "construct" means any recombinant DNA molecule such as a plasmid, cosmid, virus, phage, or linear or circular DNA or RNA molecule, derived from any source, capable of genomic integration or autonomous replication, comprising a DNA molecule where at least one DNA molecule has been linked to another DNA molecule in a functionally operative manner, i.e. operably linked. As used herein, the term "vector" means any construct that may be used for the purpose of transformation, i.e., the introduction of heterologous DNA or RNA into a host cell. A construct typically includes one or more expression cassettes. As used herein, an "expression cassette" refers to a DNA molecule comprising at least a transcribable DNA molecule operably linked to one or more regulatory elements, typically at least a promoter and a 3' UTR.

As used herein, the term "operably linked" refers to a first DNA molecule joined to a second DNA molecule, wherein the first and second DNA molecules are so arranged that the first DNA molecule affects the function of the second DNA molecule. The two DNA molecules may or may not be part of a single contiguous DNA molecule and may or may not be adjacent. For example, a promoter is operably linked to a transcribable DNA molecule if the promoter modulates transcription of the transcribable DNA molecule of interest in a cell. A leader, for example, is operably linked to DNA sequence when it is capable of affecting the transcription or translation of the DNA sequence.

The constructs of the invention may be provided, in one embodiment, as double tumor-inducing (Ti) plasmid border constructs that have the right border (RB or AGRtu.RB) and left border (LB or AGRtu.LB) regions of the Ti plasmid isolated from *Agrobacterium tumefaciens* comprising a T-DNA that, along with transfer molecules provided by the *A. tumefaciens* cells, permit the integration of the T-DNA into the genome of a plant cell (see, e.g., U.S. Pat. No. 6,603,061). The constructs may also contain the plasmid backbone DNA segments that provide replication function and antibiotic selection in bacterial cells, e.g., an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *A. tumefaciens* ABI, C58, or LBA4404, however other strains known to those skilled in the art of plant transformation can function in the invention.

Methods are known in the art for assembling and introducing constructs into a cell in such a manner that the transcribable DNA molecule is transcribed into a functional mRNA molecule that is translated and expressed as a protein. For the practice of the invention, conventional compositions and methods for preparing and using constructs and host cells are well known to one skilled in the art. Typical vectors useful for expression of nucleic acids in higher plants are well known in the art and include vectors derived from the Ti plasmid of *Agrobacterium tumefaciens* and the pCaMVCN transfer control vector.

Various regulatory elements may be included in a construct, including any of those provided herein. Any such regulatory elements may be provided in combination with other regulatory elements. Such combinations can be designed or modified to produce desirable regulatory features. In one embodiment, constructs of the invention comprise at least one regulatory element operably linked to a transcribable DNA molecule operably linked to a 3' UTR.

Constructs of the invention may include any promoter or leader provided herein or known in the art. For example, a promoter of the invention may be operably linked to a heterologous non-translated 5' leader such as one derived from a heat shock protein gene. Alternatively, a leader of the invention may be operably linked to a heterologous promoter such as the Cauliflower mosaic virus 35S transcript promoter.

Expression cassettes may also include a transit peptide coding sequence that encodes a peptide that is useful for sub-cellular targeting of an operably linked protein, particularly to a chloroplast, leucoplast, or other plastid organelle; mitochondria; peroxisome; vacuole; or an extracellular location. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, and enolpyruvyl shikimate phosphate synthase (EPSPS). Chloroplast transit peptides are described, for example, in U.S. Pat. No. 7,193,133. It has been demonstrated that non-chloroplast proteins may be targeted to the chloroplast by the expression of a heterologous CTP operably linked to the transgene encoding a non-chloroplast protein.

Transcribable DNA Molecules

As used herein, the term "transcribable DNA molecule" refers to any DNA molecule capable of being transcribed into a RNA molecule, including, but not limited to, those having protein coding sequences and those producing RNA molecules having sequences useful for gene suppression. The type of DNA molecule can include, but is not limited to, a DNA molecule from the same plant, a DNA molecule from another plant, a DNA molecule from a different organism, or a synthetic DNA molecule, such as a DNA molecule containing an antisense message of a gene, or a DNA molecule encoding an artificial, synthetic, or otherwise modified version of a transgene. Exemplary transcribable DNA molecules for incorporation into constructs of the invention include, e.g., DNA molecules or genes from a species other than the species into which the DNA molecule is incorporated or genes that originate from, or are present in, the same species, but are incorporated into recipient cells by genetic engineering methods rather than classical breeding techniques.

A "transgene" refers to a transcribable DNA molecule heterologous to a host cell at least with respect to its location in the host cell genome and/or a transcribable DNA molecule artificially incorporated into a host cell's genome in the current or any prior generation of the cell.

A regulatory element, such as a promoter, enhancer, intron, or 3' UTR of the invention, may be operably linked to a transcribable DNA molecule that is heterologous with respect to the regulatory element. As used herein, the term "heterologous" refers to the combination of two or more DNA molecules when such a combination is not normally found in nature. For example, the two DNA molecules may be derived from different species and/or the two DNA molecules may be derived from different genes, e.g., different genes from the same species or the same genes from different species. A regulatory element is thus heterologous with respect to an operably linked transcribable DNA molecule if such a combination is not normally found in nature, i.e., the transcribable DNA molecule does not naturally occur operably linked to the regulatory element.

The transcribable DNA molecule may generally be any DNA molecule for which expression of a transcript is desired. Such expression of a transcript may result in translation of the resulting mRNA molecule, and thus protein expression. Alternatively, for example, a transcribable DNA molecule may be designed to ultimately cause decreased expression of a specific gene or protein. In one embodiment, this may be accomplished by using a transcribable DNA molecule that is oriented in the antisense direction. One of ordinary skill in the art is familiar with using such antisense technology. Any gene may be negatively regulated in this manner, and, in one embodiment, a transcribable DNA molecule may be designed for suppression of a specific gene through expression of a dsRNA, siRNA or miRNA molecule.

Thus, one embodiment of the invention is a recombinant DNA molecule comprising a regulatory element of the invention, such as those provided as SEQ ID NOs:2-8, 12-14, and 16-19, operably linked to a heterologous transcribable DNA molecule so as to modulate transcription of the transcribable DNA molecule at a desired level or in a desired pattern when the construct is integrated in the genome of a transgenic plant cell. In one embodiment, the transcribable DNA molecule comprises a protein-coding region of a gene and in another embodiment the transcribable DNA molecule comprises an antisense region of a gene.

Genes of Agronomic Interest

A transcribable DNA molecule may be a gene of agronomic interest. As used herein, the term "gene of agronomic interest" refers to a transcribable DNA molecule that, when expressed in a particular plant tissue, cell, or cell type, confers a desirable characteristic. The product of a gene of agronomic interest may act within the plant in order to cause an effect upon the plant morphology, physiology, growth, development, yield, grain composition, nutritional profile, disease or pest resistance, and/or environmental or chemical tolerance or may act as a pesticidal agent in the diet of a pest that feeds on the plant. In one embodiment of the invention, a regulatory element of the invention is incorporated into a construct such that the regulatory element is operably linked to a transcribable DNA molecule that is a gene of agronomic interest. In a transgenic plant containing such a construct, the expression of the gene of agronomic interest can confer a beneficial agronomic trait. A beneficial agronomic trait may include, for example, but is not limited to, herbicide tolerance, insect control, modified yield, disease resistance, pathogen resistance, modified plant growth and development, modified starch content, modified oil content, modified fatty acid content, modified protein content, modified fruit ripening, enhanced animal and human nutrition, biopolymer productions, environmental stress resistance, pharmaceutical peptides, improved processing qualities, improved flavor, hybrid seed production utility, improved fiber production, and desirable biofuel production.

Examples of genes of agronomic interest known in the art include those for herbicide resistance (U.S. Pat. Nos. 6,803, 501; 6,448,476; 6,248,876; 6,225,114; 6,107,549; 5,866, 775; 5,804,425; 5,633,435; and 5,463,175), increased yield (U.S. Pat. Nos. USRE38,446; 6,716,474; 6,663,906; 6,476, 295; 6,441,277; 6,423,828; 6,399,330; 6,372,211; 6,235, 971; 6,222,098; and 5,716,837), insect control (U.S. Pat. Nos. 6,809,078; 6,713,063; 6,686,452; 6,657,046; 6,645, 497; 6,642,030; 6,639,054; 6,620,988; 6,593,293; 6,555, 655; 6,538,109; 6,537,756; 6,521,442; 6,501,009; 6,468, 523; 6,326,351; 6,313,378; 6,284,949; 6,281,016; 6,248, 536; 6,242,241; 6,221,649; 6,177,615; 6,156,573; 6,153, 814; 6,110,464; 6,093,695; 6,063,756; 6,063,597; 6,023, 013; 5,959,091; 5,942,664; 5,942,658, 5,880,275; 5,763, 245; and 5,763,241), fungal disease resistance (U.S. Pat. Nos. 6,653,280; 6,573,361; 6,506,962; 6,316,407; 6,215, 048; 5,516,671; 5,773,696; 6,121,436; 6,316,407; and 6,506,962), virus resistance (U.S. Pat. Nos. 6,617,496; 6,608,241; 6,015,940; 6,013,864; 5,850,023; and 5,304, 730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; 6,476,295), modified oils production (U.S. Pat. Nos. 6,444,876; 6,426,447; and 6,380, 462), high oil production (U.S. Pat. Nos. 6,495,739; 5,608, 149; 6,483,008; and 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; and 6,459,018), high protein production (U.S. Pat. No. 6,380, 466), fruit ripening (U.S. Pat. No. 5,512,466), enhanced animal and human nutrition (U.S. Pat. Nos. 6,723,837; 6,653,530; 6,5412,59; 5,985,605; and 6,171,640), biopolymers (U.S. Pat. Nos. USRE37,543; 6,228,623; and 5,958, 745, and 6,946,588), environmental stress resistance (U.S. Pat. No. 6,072,103), pharmaceutical peptides and secretable peptides (U.S. Pat. Nos. 6,812,379; 6,774,283; 6,140,075; and 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229, 114), hybrid seed production (U.S. Pat. No. 5,689,041), fiber production (U.S. Pat. Nos. 6,576,818; 6,271,443; 5,981,834; and 5,869,720) and biofuel production (U.S. Pat. No. 5,998, 700).

Alternatively, a gene of agronomic interest can affect the above mentioned plant characteristics or phenotypes by encoding a RNA molecule that causes the targeted modulation of gene expression of an endogenous gene, for example by antisense (see, e.g. U.S. Pat. No. 5,107,065); inhibitory RNA ("RNAi," including modulation of gene expression by miRNA-, siRNA-, trans-acting siRNA-, and phased sRNA-mediated mechanisms, e.g., as described in published applications U.S. 2006/0200878 and U.S. 2008/0066206, and in U.S. patent application Ser. No. 11/974,469); or cosuppression-mediated mechanisms. The RNA could also be a catalytic RNA molecule (e.g., a ribozyme or a riboswitch; see, e.g., U.S. 2006/0200878) engineered to cleave a desired endogenous mRNA product. Methods are known in the art for constructing and introducing constructs into a cell in such a manner that the transcribable DNA molecule is transcribed into a molecule that is capable of causing gene suppression.

Selectable Markers

Selectable marker transgenes may also be used with the regulatory elements of the invention. As used herein the term "selectable marker transgene" refers to any transcribable DNA molecule whose expression in a transgenic plant, tissue or cell, or lack thereof, can be screened for or scored in some way. Selectable marker genes, and their associated selection and screening techniques, for use in the practice of the invention are known in the art and include, but are not limited to, transcribable DNA molecules encoding β-glucuronidase (GUS), green fluorescent protein (GFP), proteins that confer antibiotic resistance, and proteins that confer herbicide tolerance. An example of a selectable marker transgenes is provided as SEQ ID NO:11.

Cell Transformation

The invention is also directed to a method of producing transformed cells and plants that comprise one or more regulatory elements operably linked to a transcribable DNA molecule.

The term "transformation" refers to the introduction of a DNA molecule into a recipient host. As used herein, the term "host" refers to bacteria, fungi, or plants, including any cells, tissues, organs, or progeny of the bacteria, fungi, or plants. Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign DNA molecule, such as a construct, has been introduced. The introduced DNA molecule may be integrated into the genomic DNA of the recipient cell, tissue, organ, or organism such that the introduced DNA molecule is inherited by subsequent progeny. A "transgenic" or "transformed" cell or organism may also include progeny of the cell or organism and progeny produced from a breeding program employing such a transgenic organism as a parent in a cross and exhibiting an altered phenotype resulting from the presence of a foreign DNA molecule. The introduced DNA molecule may also be transiently introduced into the recipient cell such that the introduced DNA molecule is not inherited by subsequent progeny. The term "transgenic" refers to a bacterium, fungus, or plant containing one or more heterologous DNA molecules.

There are many methods well known to those of skill in the art for introducing DNA molecules into plant cells. The process generally comprises the steps of selecting a suitable host cell, transforming the host cell with a vector, and obtaining the transformed host cell. Methods and materials for transforming plant cells by introducing a plant construct into a plant genome in the practice of this invention can include any of the well-known and demonstrated methods. Suitable methods include, but are not limited to, bacterial infection (e.g., *Agrobacterium*), binary BAC vectors, direct delivery of DNA (e.g., by PEG-mediated transformation, desiccation/inhibition-mediated DNA uptake, electroporation, agitation with silicon carbide fibers, and acceleration of DNA coated particles), gene editing (e.g., CRISPR-Cas systems), among others.

Host cells may be any cell or organism, such as a plant cell, algal cell, algae, fungal cell, fungi, bacterial cell, or insect cell. In specific embodiments, the host cells and transformed cells may include cells from crop plants.

A transgenic plant subsequently may be regenerated from a transgenic plant cell of the invention. Using conventional breeding techniques or self-pollination, seed may be produced from this transgenic plant. Such seed, and the resulting progeny plant grown from such seed, will contain the recombinant DNA molecule of the invention, and therefore will be transgenic.

Transgenic plants of the invention can be self-pollinated to provide seed for homozygous transgenic plants of the invention (homozygous for the recombinant DNA molecule) or crossed with non-transgenic plants or different transgenic plants to provide seed for heterozygous transgenic plants of the invention (heterozygous for the recombinant DNA molecule). Both such homozygous and heterozygous transgenic plants are referred to herein as "progeny plants." Progeny plants are transgenic plants descended from the original transgenic plant and containing the recombinant DNA molecule of the invention. Seeds produced using a transgenic plant of the invention can be harvested and used to grow generations of transgenic plants, i.e., progeny plants of the invention, comprising the construct of this invention and expressing a gene of agronomic interest. Descriptions of breeding methods that are commonly used for different crops can be found in one of several reference books, see, e.g., Allard, *Principles of Plant Breeding*, John Wiley & Sons, NY, U. of CA, Davis, Calif., 50-98 (1960); Simmonds, *Principles of Crop Improvement*, Longman, Inc., NY, 369-399 (1979); Sneep and Hendriksen, *Plant breeding Perspectives*, Wageningen (ed), Center for Agricultural Publishing and Documentation (1979); Fehr, *Soybeans: Improvement, Production and Uses,* 2nd Edition, Monograph, 16:249 (1987); Fehr, *Principles of Variety Development, Theory and Technique*, (Vol. 1) and *Crop Species Soybean* (Vol. 2), Iowa State Univ., Macmillan Pub. Co., NY, 360-376 (1987).

The transformed plants may be analyzed for the presence of the gene or genes of interest and the expression level and/or profile conferred by the regulatory elements of the invention. Those of skill in the art are aware of the numerous methods available for the analysis of transformed plants. For example, methods for plant analysis include, but are not limited to, Southern blots or northern blots, PCR-based approaches, biochemical analyses, phenotypic screening methods, field evaluations, and immunodiagnostic assays. The expression of a transcribable DNA molecule can be measured using TaqMan® (Applied Biosystems, Foster City, Calif.) reagents and methods as described by the manufacturer and PCR cycle times determined using the TaqMan® Testing Matrix. Alternatively, the Invader® (Third Wave Technologies, Madison, Wis.) reagents and methods as described by the manufacturer can be used to evaluate transgene expression.

The invention also provides for parts of a plant of the invention. Plant parts include, but are not limited to, leaves, stems, roots, tubers, seeds, endosperm, ovule, and pollen. Plant parts of the invention may be viable, nonviable, regenerable, and/or non-regenerable. The invention also includes and provides transformed plant cells comprising a DNA molecule of the invention. The transformed or transgenic plant cells of the invention include regenerable and/or non-regenerable plant cells.

The invention also provides a commodity product that is produced from a transgenic plant or part thereof containing the recombinant DNA molecule of the invention. Commodity products of the invention contain a detectable amount of DNA comprising a DNA sequence selected from the group consisting of SEQ ID NOs:2-8, 12-14, and 16-19. As used herein, a "commodity product" refers to any composition or product which is comprised of material derived from a transgenic plant, seed, plant cell, or plant part containing the recombinant DNA molecule of the invention. Commodity products include but are not limited to processed seeds, grains, plant parts, and meal. A commodity product of the invention will contain a detectable amount of DNA corresponding to the recombinant DNA molecule of the invention. Detection of one or more of this DNA in a sample may be used for determining the content or the source of the commodity product. Any standard method of detection for DNA molecules may be used, including methods of detection disclosed herein.

The invention may be more readily understood through reference to the following examples, which are provided by way of illustration, and are not intended to be limiting of the invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth is to be interpreted as illustrative and not in a limiting sense.

EXAMPLES

Example 1

Identification and Cloning of Regulatory Elements

Novel transcriptional regulatory elements and a regulatory expression element group (EXPs) were identified and cloned from genomic DNA of several monocot species.

The novel three prime untranslated region (3' UTRs) sequences were identified in proprietary sequences of several monocot species. Table 1 below shows the different 3' UTRs and the monocot species from which they were derived. The 3' UTR, T-SETit.Ams1:1 (SEQ ID NO:1) has been previously presented as SEQ ID NO:270 in United States Patent Application US20130031672.

TABLE 1

3' UTRs and corresponding Genus and species.

| Description | SEQ ID NO: | Genus/species |
|---|---|---|
| T-SETit.Ams1:1 | 1 | Setaria italica |
| T-Cl.Hsp16.9_2:1 | 2 | Coix lacrytna-jobi |
| T-ERAte.Hsp17.9:1 | 3 | Eragrostis tef |
| T-ERIra.Hsp16.9_3:1 | 4 | Saccharum ravennae |
| T-ANDge.Hsp/Sb.Hsp | 5 | Chimera derived from Andropogon gerardii/Sorghum bicolor |

TABLE 1-continued

3' UTRs and corresponding Genus and species.

| Description | SEQ ID NO: | Genus/species |
|---|---|---|
| T-SACra.Hsp16.9:2 | 12 | Saccharum ravennae |
| T-Cl.Hsp16.9:2 | 13 | Coix lacrytna-jobi |

In addition, an EXP sequence comprising a promoter (P-Zm.Ltp-1:1:2) and leader (L-Zm.Ltp-1:1:3) isolated from Zea mays genomic DNA and an intron isolated from Setaria italic genomic DNA was created and cloned. The EXP, EXP-Zm.LTP-SETit.Act4 (SEQ ID NO:6), is comprised of the promoter, P-Zm.Ltp-1:1:2 (SEQ ID NO:7), operably linked 5' to the 5' UTR, L-Zm.Ltp-1:1:3 (SEQ ID NO:8), operably linked 5' to the intron, I-SETit.Act4:2 (SEQ ID NO:9; previously presented as SEQ ID NO:627 in United States Patent Application US20130031672).

These 3' UTRs and the EXP-Zm.LTP-SETit.Act4 were cloned into binary plant transformation vectors using methods known in the art.

Example 2

Analysis of the 3' UTRs and Their Effect on Expression of a Transgene in Stably Transformed Corn Plants Corn plants were transformed with vectors, specifically plant expression vectors containing transcriptional regulatory elements driving expression of the β-glucuronidase (GUS) transgene and one of each of the seven (7) 3' UTR regulatory elements presented in Example 1. The resulting plants were analyzed for GUS protein expression, to assess the effect of the 3' UTR regulatory elements on expression.

Corn plants were transformed with plant GUS expression constructs. The 3' UTR regulatory elements were cloned into a base plant expression vector using methods known in the art. The resulting plant expression vectors contained a left border region from Agrobacterium tumefaciens, a first transgene selection cassette used for selection of transformed plant cells that confers resistance to the herbicide glyphosate; a second transgene cassette to assess the activity of the 3' UTR regulatory elements, which comprised an enhancer derived from the Cauliflower mosaic virus 35S promoter in reverse compliment orientation (E-CaMV.35S-RC, SEQ ID NO:10), operably linked 5' to the EXP, EXP-Zm.LTP-SETit.Act4 (SEQ ID NO:6), operably linked 5' to a synthetic coding sequence designed for expression in a plant cell encoding β-glucuronidase (GUS, GOI-Ec.uidA+St.LS1.nno:1, SEQ ID NO:11) containing a processable intron derived from the potato light-inducible tissue-specific ST-LS1 gene (Genbank Accession: X04753), operably linked 5' to one of each of the seven (7) 3' UTR regulatory elements presented in Example 1, followed by a right border region from Agrobacterium tumefaciens.

Corn plant cells from corn variety 01DKD2 were transformed using these binary transformation vector constructs by Agrobacterium-mediated transformation, as is well known in the art. The resulting transformed plant cells were induced to form whole corn plants.

Histochemical GUS analysis was used for qualitative and quantitative expression analysis of transformed plants. Whole tissue sections were incubated with GUS staining solution X-Gluc (5-bromo-4-chloro-3-indolyl-b-glucuronide) (1 milligram/milliliter) for an appropriate length of time, rinsed, and visually inspected for blue coloration.

GUS activity was qualitatively determined by direct visual inspection or inspection under a microscope using selected plant organs and tissues.

For quantitative analysis of GUS expression, total protein was extracted from selected tissues of transformed corn plants. One microgram of total protein was used with the fluorogenic substrate 4-methyleumbelliferyl-β-D-glucuronide (MUG) in a total reaction volume of 50 microliters. The reaction product, 4-methylumbelliferone (4-MU), is maximally fluorescent at high pH, where the hydroxyl group is ionized. Addition of a basic solution of sodium carbonate simultaneously stops the assay and adjusts the pH for quantifying the fluorescent product. Fluorescence was measured with excitation at 365 nm, emission at 445 nm using a FLUOstar® Omega microplate reader. Values are provided in units of nmol GUS/hour/mg total protein.

The following tissues were sampled for GUS expression for five (5) of the 3' UTR regulatory elements presented in Example 1 in the $R_0$ generation: V4 stage leaf and root; V7 stage leaf and root; VT stage flower/anther, leaf, and root; R1 stage Cob and silk; R3 stage 21 days after pollination (DAP) seed embryo and endosperm. Tables 2 and 3 below show the effect of each of the 3' UTR regulatory elements on the expression of GUS.

root expression. Expression in roots using T-Cl.Hsp16.9_2:1 was similarly high as corn plants comprising T-SETit.Ams1:1, but leaf expression was higher in plants comprising T-Cl.Hsp16.9_2:1 when compared to corn plants comprising T-SETit.Ams1:1. Root expression was lower in corn plants comprising T-ERIra.Hsp16.9_3:1 at V4 stage, but increased progressively from V7 to VT stage. With respect to VT Flower and Anther, R1 Cob and Silk, and 21 DAP Embryo, expression was highest in corn plants comprising T-Cl.Hsp16.9_2:1 in comparison to the other four 3' UTR regulatory elements. Expression in 21 DAP Endosperm was highest in corn plants comprising T-SETit.Ams1:1 in comparison to the other four 3' UTR regulatory elements.

Corn plants were also transformed with plant GUS expression constructs as described above comprising two of the 3' UTR regulatory elements presented in Example 1, T-SACra.Hsp16.9:2 (SEQ ID NO:12) and T-Cl.Hsp16.9:2 (SEQ ID NO:13). GUS expression was determined as described above. Only V2 stage leaves and roots were sampled. Table 4 below shows the average GUS expression for corn plants stably transformed with constructs comprising the two 3' UTR regulatory elements.

TABLE 2

Effect of 3' UTR regulatory elements on the quantitative GUS expression in stably transformed $R_0$ corn plants.

| Description | SEQ ID NO: | V4 Root | V4 Leaf | V7 Root | V7 Leaf | VT Root | VT Leaf | VT Flower/Anther |
|---|---|---|---|---|---|---|---|---|
| T-SETit.Ams1:1 | 1 | 4017 | 303 | 2639 | 90 | 3862 | 213 | 249 |
| T-Cl.Hsp16.9_2:1 | 2 | 4125 | 1491 | 3895 | 541 | 4842 | 2006 | 456 |
| T-ERAte.Hsp17.9:1 | 3 | 1817 | 247 | 2387 | 263 | 3863 | 493 | 142 |
| T-ERIra.Hsp16.9_3:1 | 4 | 4995 | 1181 | 2217 | 476 | 2982 | 1022 | 395 |
| T-ANDge.Hsp/Sb.Hsp | 5 | 2892 | 583 | 1561 | 238 | 2750 | 537 | 296 |

TABLE 3

Effect of 3' UTR regulatory elements on the quantitative GUS expression in stably transformed $R_0$ corn plants.

| Description | SEQ ID NO: | R1 Cob/Silk | 21 DAP Embryo | 21 DAP Endosperm |
|---|---|---|---|---|
| T-SETit.Ams1:1 | 1 | 1818 | 1254 | 638 |
| T-Cl.Hsp16.9_2:1 | 2 | 4690 | 2403 | 176 |
| T-ERAte.Hsp17.9:1 | 3 | 1266 | 578 | 285 |
| T-ERIra.Hsp16.9_3:1 | 4 | 1162 | 921 | 84 |
| T-ANDge.Hsp/Sb.Hsp | 5 | 2031 | 1353 | 140 |

As can be seen in Tables 2 and 3, each 3' UTR regulatory element affected expression uniquely in each of the tissues sampled, when operably linked to the same enhancer/promoter/intron construct combination. The promoter P-Zm.Ltp-1:1:2 has been experimentally determined to express preferentially in the roots. The addition of the enhancer, E-CaMV.35S-RC, adds a constitutive expression component. Each of the 3' UTR regulatory elements modulates the expression imparted by the enhancer/promoter/intron construct combination. For example, the 3' UTR, T-SETit.Ams1:1 enhanced root expression of the construct relative to T-ERAte.Hsp17.9:1 and T-ANDge.Hsp/Sb.Hsp. Leaf expression using T-SETit.Ams1:1 was much lower than

TABLE 4

Effect of 3' UTR regulatory elements on the quantitative GUS expression in stably transformed $R_0$ corn plants.

| Description | SEQ ID NO: | V2 Leaf | V2 Root |
|---|---|---|---|
| T-SACra.Hsp16.9:2 | 12 | 987.66 | 6226.99 |
| T-Cl.Hsp16.9:2 | 13 | 789.07 | 3299.47 |

As can be seen in Table 4 above, T-SACra.Hsp16.9:2 (SEQ ID NO:12) provided overall higher levels of GUS expression in root and leaf when compared to T-Cl.Hsp16.9:2 (SEQ ID NO:13). Expression was approximately 6.3 fold higher in root than in leaf for T-SACra.Hsp16.9:2. In comparison, the ratio of root to leaf expression for T-Cl.Hsp16.9:2 was lower than that of T-SACra.Hsp16.9:2 at approximately 4.2 fold.

Each of the seven (7) 3' UTR regulatory elements presented above were able to modulate expression of the GUS transgene to provide unique patterns of gene expression in different tissues. These unique expression patterns can be used to fine tune expression of specific transgenes of interest to provide an expression profile in certain preferred tissues while reducing expression in other less preferred tissues. Each of the seven 3' UTR regulatory elements provide a great deal of flexibility for driving certain traits in transgenic plants.

Example 3

Analysis of EXP-Zm.LTP-SETit.Act4 on Expression of a Transgene in Stably Transformed Corn Plants Corn plants were transformed with a vector, specifically a plant expression vector containing transcriptional regulatory elements driving expression of the β-glucuronidase (GUS) transgene. The resulting plants were analyzed for GUS protein expression, to assess the expression properties of the EXP, EXP-Zm.LTP-SETit.Act4 (SEQ ID NO:6).

Corn plants were transformed with a plant GUS expression construct. The EXP, EXP-Zm.LTP-SETit.Act4 (SEQ ID NO:6) was cloned into a base plant expression vector using methods known in the art. The resulting plant expression vector contained a left border region from *Agrobacterium tumefaciens*, a first transgene selection cassette used for selection of transformed plant cells that confers resistance to the herbicide glyphosate; a second transgene cassette to assess the activity of EXP-Zm.LTP-SETit.Act4, which comprises the EXP, EXP-Zm.LTP-SETit.Act4, operably linked 5' to a synthetic coding sequence designed for expression in a plant cell encoding β-glucuronidase (GUS, GOI-Ec.uidA+St.LS1.nno:1), operably linked 5' to the 3' UTR regulatory element, T-SETit.Ams1:1, followed by a right border region from *Agrobacterium tumefaciens*.

Corn plant cells from corn variety 01DKD2 were transformed using the binary transformation vector constructs described above by *Agrobacterium*-mediated transformation, as is well known in the art. The resulting transformed plant cells were induced to form whole corn plants. Quantitative and qualitative measurements of GUS expression was determined as described in the previous example using V2 stage leaf and root Table 5 shows the average GUS expression for the stably transformed V2 leaves and roots and ratio of GUS expression of root compared to leaf.

TABLE 5

Average GUS expression and ratio of expression in V2 leaves and roots driven by EXP-Zm.LTP-SETit.Act4 in stably transformed corn plants.

EXP-Zm.LTP-SETit.Act4

| Leaf | Root | R/L Ratio |
| --- | --- | --- |
| 242.27 | 8513.02 | 35.14 |

As can be seen in Table 5, GUS expression driven by EXP-Zm.LTP-SETit.Act4 is much higher in the root than in leaf. Root expression is more than thirty-five (35) times that measured in leaf. This expression pattern may be advantageous in driving certain transgenes where root expression in more preferred than above ground expression.

Example 4

Enhancer Orientation Affects the Ratio of Expression Between Roots and Leaves in Stably Transformed Corn Plants This example illustrates the effect of operably linking a Dahlia mosaic virus enhancer in different orientations to a promoter, altering the relative expression of a transgene in leaves and roots. Corn plants were transformed with plant expression vectors containing an EXP that comprised an enhancer in a forward or reverse orientation relative to a native promoter comprising the enhancer sequence. The resulting plants were analyzed to determine the effect of the enhancer's orientation on GUS protein expression in roots and leaves.

Corn plants were transformed with plant GUS expression constructs. The EXPs, EXP-DaMV.H-Flt+Zm.Ltp+SETit.Act4:1 (SEQ ID NO:16), EXP-DaMV.H-Flt+Zm.Ltp+Zm.Ltp+SETit.Act4:4 (SEQ ID NO:17), EXP-DaMV.FLT+Td.RCc3_1+SETit.14-3-3C-5:1 (SEQ ID NO:18), and EXP-DaMV.FLT+Td.RCc3_1+Td.RCc3_1+SETit.14-3-3C-5:5 (SEQ ID NO:19) were cloned into a base plant expression vector using methods known in the art. The resulting plant expression vector contained a left border region from *Agrobacterium tumefaciens*, a first transgene selection cassette used for selection of transformed plant cells that confers resistance to the herbicide glyphosate; a second transgene cassette to assess the activity of the EXPs presented above, operably linked 5' to a synthetic coding sequence designed for expression in a plant cell encoding β-glucuronidase (GUS, GOI-Ec.uidA+St.LS1.nno:1), operably linked 5' to the 3' UTR regulatory element, T-SETit.Ams1:1, followed by a right border region from *Agrobacterium tumefaciens*.

Each of the EXPs comprised an enhancer derived from Dahlia mosaic virus promoters. The enhancers were operably linked 5' to the respective promoter of each EXP in either the forward orientation (the orientation of the enhancer within the native promoter in the Dahlia mosaic virus genome) or the reverse orientation (the opposite orientation of the enhancer within the native promoter in the Dahlia mosaic virus genome). The EXPs, EXP-DaMV.H-Flt+Zm.Ltp+SETit.Act4:1 (SEQ ID NO:16) and EXP-DaMV.H-Flt+Zm.Ltp+Zm.Ltp+SETit.Act4:4 (SEQ ID NO:17) comprised a chimeric-rearranged enhancer, E-DaMV.H-Flt:1 (SEQ ID NO:14), derived from multiple public Dahlia mosaic virus promoters. A first fragment was derived from the promoter of the DaMV-Holland (DaMV-H) strain, Genbank accession EU090957, nucleotides 1177-1494. This fragment was operably linked to a second fragment derived from the DaMV-H promoter, nucleotides 1003-1176. In the native DaMV promoter configuration, the second fragment would precede the first fragment. Within the first fragment, relative to SEQ ID NO:14, nucleotides 287 through 288, and nucleotides 319 through 322 were changed to sequences in analogous locations of a DaMV promoter within Genbank accession JX272320. The EXPs, EXP-DaMV.FLT+Td.RCc3_1+SETit.14-3-3C-5:1 (SEQ ID NO:18) and EXP-DaMV.FLT+Td.RCc3_1+Td.RCc3_1+SETit.14-3-3C-5:5 (SEQ ID NO:19) comprised an enhancer, E-DaMV.FLT:2 (SEQ ID NO:15), derived from a Dalia mosaic virus promoter, Genbank accession EF513491, nucleotides 1 through 322.

The EXPs, EXP-DaMV.H-Flt+Zm.Ltp+SETit.Act4:1 (SEQ ID NO:16) and EXP-DaMV.H-Flt+Zm.Ltp+Zm.Ltp+SETit.Act4:4 (SEQ ID NO:17) comprise a chimeric-rearranged enhancer, E-DaMV.H-Flt:1 (SEQ ID NO:14), operably linked 5' to the promoter and 5' UTR derived from a lipid transfer protein-like protein gene from *Zea mays*, operably linked 5' to an intron derived from an actin 4 gene from *Setaria italica*. The EXPs, EXP-DaMV.FLT+Td.RCc3_1+SETit.14-3-3C-5:1 (SEQ ID NO:18) and EXP-DaMV.FLT+Td.RCc3_1+Td.RCc3_1+SETit.14-3-3C-5:5 (SEQ ID NO:19) comprise an enhancer, E-DaMV.FLT:2 (SEQ ID NO:15), operably linked 5' to the promoter and 5' UTR derived from an RCc3 gene from *Trypsicum dactyloides*, operably linked 5' to an intron derived from a 14-3-3C gene from *Setaria italica*.

Corn plant cells from corn variety 01DKD2 were transformed using the binary transformation vector constructs described above by *Agrobacterium*-mediated transformation, as is well known in the art. The resulting transformed plant cells were induced to form whole corn plants. Quantitative and qualitative measurements of GUS expression was determined as described in Example 2 using V2 stage leaf and root. Table 6 shows the average GUS expression for the stably transformed V2 leaves and roots for each of the four (4) EXPs. The orientation of the enhancer and the ratio of root to leaf expression is also shown in Table 6.

TABLE 6

Average GUS expression, enhancer orientation, and the ratio of root to leaf expression in V2 leaves and roots driven by the EXPs in stably transformed corn plants.

| EXP | SEQ ID NO: | Enhancer Orientation | Average GUS Leaf | Average GUS Root | R/L Ratio |
| --- | --- | --- | --- | --- | --- |
| EXP-DaMV.H-Flt + Zm.Ltp + SETit.Act4:1 | 16 | Reverse | 3634 | 9896 | 2.72 |
| EXP-DaMV.H-Flt + Zm.Ltp + Zm.Ltp + SETit.Act4:4 | 17 | Forward | 4486 | 9545 | 2.13 |
| EXP-DaMV.FLT + Td.RCc3_1 + SETit.14-3-3C-5:1 | 18 | Reverse | 6599 | 12392 | 1.88 |
| EXP-DaMV.FLT + Td.RCc3_1 + Td.RCc3_1 + SETit.14-3-3C-5:5 | 19 | Forward | 6013 | 9201 | 1.53 |

In Example 3, Table 5, the EXP, EXP-Zm.LTP-SETit.Act4 (SEQ ID NO:6) drove expression of GUS much higher in roots than leaves by more than thirty-five (35) fold. As shown in Table 6, by operably linking the chimeric-rearranged enhancer, E-DaMV.H-Flt:1 (SEQ ID NO:14) 5' to the promoter within EXP-Zm.LTP-SETit.Act4 that is comprised within EXP-DaMV.H-Flt+Zm.Ltp+SETit.Act4:1 (SEQ ID NO:16) and EXP-DaMV.H-Flt+Zm.Ltp+Zm.Ltp+ SETit.Act4:4 (SEQ ID NO:17), GUS expression increased in the leaf relative to the root. However, the orientation of the enhancer within these two EXPs affected the relative levels of GUS expression in the root and leaves. The ratio of root to leaf expression was higher when the E-DaMV.H-Flt:1 was oriented in the reverse orientation in comparison to the forward orientation. Likewise, operably linking the E-DaMV.FLT:2 (SEQ ID NO:15) enhancer within EXP-DaMV.FLT+Td.RCc3_1+SETit.14-3-3C-5:1 (SEQ ID NO:18) in the reverse orientation resulted in a higher root to leaf GUS expression ratio when compared to the forward orientation within EXP-DaMV.FLT+Td.RCc3_1+ Td.RCc3_1+SETit.14-3-3C-5:5 (SEQ ID NO:19). By operably linking the two enhancers in the reverse orientation, one can provide an expression profile that provides a higher root to leaf expression ratio than when the enhancers are operably linked in the forward orientation. This feature is desirable for when one wants to boost expression using a viral enhancer, but would prefer providing the highest root to leaf expression ratio possible.

Having illustrated and described the principles of the present invention, it should be apparent to persons skilled in the art that the invention can be modified in arrangement and detail without departing from such principles. We claim all modifications that are within the spirit and scope of the claims. All publications and published patent documents cited herein are hereby incorporated by reference to the same extent as if each individual publication or patent application is specifically and individually indicated to be incorporated by reference.

What is claimed is:

1. A recombinant DNA molecule comprising a DNA sequence selected from the group consisting of:
   a) a sequence with at least 98 percent sequence identity to SEQ ID NO: 14 and having enhancer activity;
   b) a sequence comprising SEQ ID NO: 14; and
   c) a fragment comprising at least 250 contiguous nucleotides of SEQ ID NO: 14, wherein the fragment has enhancer activity;
   wherein said sequence is operably linked to a heterologous transcribable DNA molecule.

2. The recombinant DNA molecule of claim 1, wherein said sequence has at least 99 percent sequence identity to the DNA sequence of SEQ ID NO: 14.

3. The recombinant DNA molecule of claim 1, wherein said sequence comprises the DNA sequence of SEQ ID NO: 14.

4. The recombinant DNA molecule of claim 1, wherein the DNA sequence comprises the activity of SEQ ID NO: 14.

5. The recombinant DNA molecule of claim 1, wherein the heterologous transcribable DNA molecule comprises a gene of agronomic interest.

6. The recombinant DNA molecule of claim 5, wherein the gene of agronomic interest confers herbicide tolerance in plants.

7. The recombinant DNA molecule of claim 5, wherein the gene of agronomic interest confers pest resistance in plants.

8. The recombinant DNA molecule of claim 1, wherein the heterologous transcribable DNA molecule encodes an dsRNA, an miRNA, or a siRNA.

9. A transgenic plant cell comprising the recombinant DNA molecule of claim 1.

10. The transgenic plant cell of claim 9, wherein said transgenic plant cell is a monocotyledonous plant cell.

11. The transgenic plant cell of claim 9, wherein said transgenic plant cell is a dicotyledonous plant cell.

12. A transgenic plant, or part thereof, comprising the recombinant DNA molecule of claim 1.

13. A progeny plant of the transgenic plant of claim 12, or a part thereof, wherein the progeny plant or part thereof comprises said recombinant DNA molecule.

14. A transgenic seed, wherein the seed comprises the recombinant DNA molecule of claim 1.

15. A method of producing a commodity product comprising obtaining a transgenic plant or part thereof according to claim 12 and producing the commodity product therefrom.

16. The method of claim 15, wherein the commodity product is seeds, processed seeds, protein concentrate, protein isolate, starch, grains, plant parts, seed oil, biomass, flour and meal.

17. A method of expressing a transcribable DNA molecule comprising obtaining a transgenic plant comprising the recombinant DNA molecule of claim 1 and cultivating plant, wherein the transcribable DNA is expressed.

* * * * *

SEQUENCE LISTING

```
<160> NUMBER OF SEQ ID NOS: 19

<210> SEQ ID NO 1
<211> LENGTH: 435
<212> TYPE: DNA
<213> ORGANISM: Setaria italica
<220> FEATURE:
<221> NAME/KEY: misc_feature
<222> LOCATION: (1)..(435)
<223> OTHER INFORMATION: DNA sequence of the 3' UTR, T-SETit.Ams1:1,
      derived from the S-adenosylmethionine synthetase 1 protein gene
      from Setaria italica (Foxtail millet).

<400> SEQUENCE: 1
ggcgcccttt gagaagaagc ttttggtctg ctgcgcttat catgttttgt ggcttctgtg      60
ttgtgattct tgatctgccc cttgctatca tttgtattgt actgtcctaa taagtggtac     120
```

```
ttgtgagggt attactgtgt ctggttattt acctagagga ggaattattg tctgctatttt      180 ctggttttgc tgtttatgta atggtgaacc aaagaatgaa gctgcaggct actttgagaa      240 ggaagggggac ctgctgcttt ctatcttgtc atgcgtgatt acttgaacag tcctgatgat      300
ctattaatgt tctttggtca gtgcaagtgt ttggtgtagc tccaacaggt agtgtttatg      360
tttggtgaag cagcaatggc cgactgtatg tgtttggtga agctgcaacc tgcttgtgct      420
aactgaacat gcaga                                                        435
```

<210> SEQ ID NO 2
<211> LENGTH: 561
<212> TYPE: DNA
<213> ORGANISM: Coix lacryma-jobi
<220> FEATURE:
<221> NAME/KEY: misc_feature
<222> LOCATION: (1)..(561)
<223> OTHER INFORMATION: DNA sequenced of the 3' UTR, T-Cl.Hsp16.9_2:1,
      derived from the Hsp16.9 (heat shock protein 16.9) protein gene
      from Coix lacryma-jobi (Job's tears).

<400> SEQUENCE: 2

```
atgaagtgcc atcatgccat ggatgcgggg tgaaagctcg cggcgtcgaa tataatctcc      60
ggttccagtt tcagctacta tggcgactcg tgtcgtgtgt gtgtggttac tctgcttttg     120 tatgttttggt aatggtgtgt gcgctgttgt ccagagtttc atggtggtac tgcttcctag    180
cagtgttgtg tactagtctc ggtactttgc ctgtatgttg agctcggctc agtatgttct    240
gggagtgaat aaataaaaat aaaaaaaacc agatattgta gtatactaac tgccgttgct    300
ctgtttcatc cacatacaca gaatcctatg aactgatctt tgtggggact tgggagccat    360
ctgctcggat cttcttcatg ggattctctc aatttctcct catttttcta aggctgtgtg    420
tttagatgta gggagaaaag ttttggatt gtacatcgtg ttgggtacta atttagtcta    480
ctactccgtc cgtgaataga tgcattttc tttcggtgtt gttcgtcgtg ccacaaagtt    540
ttgaatttat ttatatgcaa t                                                561
```

<210> SEQ ID NO 3
<211> LENGTH: 499
<212> TYPE: DNA
<213> ORGANISM: Eragrostis tef
<220> FEATURE:
<221> NAME/KEY: misc_feature
<222> LOCATION: (1)..(499)
<223> OTHER INFORMATION: DNA sequence of the 3' UTR,
      T-ERIra.Hsp17.9_3:1, derived from a putative heat shock protein
      gene from Eragrostis tef (Tef).

<400> SEQUENCE: 3

```
tcgatcggcg cggaggcggc tctctgttct cgcacgctgt tgatgcgtaa aacggactag      60
tatcggacgg tgtgcgacga cagtgagata tcagcagttt cctcctgtcg taagctttat     120
ttctgccctg gtttgttgga ctttgtcttc attttcatcg acctcttcct cctgcatgta    180
aaaagaagaa gaaaatagcc atgcgcggtg tgtttcctct gttcttcgtg cttagtaaat    240
gaaaagcaag ctaagctgga acctttcgtt ctctactact cctaatttct tggcatcgta    300
caattgatca gaaaaaaagc tttgttccct ggtttggtct ttgttttctg tgtgatcgat    360
ctgcctgctg catgtaaaac gaatatgaaa atgtccctgt gctatgtagt tcctctgtct    420
tttgtgctta gaaatgaag agcaacctag gcttgaagcg ttctctgcaa ctaatttctt     480
ggcatcgttc gtgcaagag                                                   499
```

```
<210> SEQ ID NO 4
<211> LENGTH: 680
<212> TYPE: DNA
<213> ORGANISM: Saccharum ravennae
<220> FEATURE:
<221> NAME/KEY: misc_feature
<222> LOCATION: (1)..(680)
<223> OTHER INFORMATION: DNA sequence of the 3' UTR,
      T-ERIra.Hsp16.9_3:1, derived from the Hsp16.9 (Heat shock protein
      16.9) protein gene from Saccharum ravennae (hardy pampas grass).

<400> SEQUENCE: 4
gcatccatag acgtggattg aaggtgtact actgctgtgc tggtccgtgg ctgtcctgca        60
cggtttattt gcactgtggc ggaggatgtt tgctgtgtct tctacgatat gtactactac       120 ttcccctttgt tccgtatatg tacatcttcc tcgtgtggtt catgtatttt ccctttgaat      180
aataataaat aaaatcaggt tttccatatc ggatcggttg cttgtatttg tgtatggaga       240 tgtggtgta tagtttcatc tcagattgtt tacgtcaaga attcaagata taatcaatgt        300
catcaaccta actcatttcc atctctagac aagcacttct gttaatcagg gagagcacat       360
gcaggctaca ctgctcgcct atatactccc tccgtcctag aaaggatgga attctcaaat      420
tttaaggtga gattagcgga gacgcgagat tacgcatgta aatttcaagg tgagattagc      480
ggagacgcga gattacgcat gtacccctgc tctccatcat tgcatctgga cttctggaga     540
attctttaca agttcattgc atctaatgcc ataagacacc cagggtgacg tgggccaaca      600
acagccacgc aatatacaca gtcacatttt ttacaaatca agtatggta gaagccaaaa       660 taaccatgac cacacatttc                                                  680

<210> SEQ ID NO 5
<211> LENGTH: 322
<212> TYPE: DNA
<213> ORGANISM: Artificial
<220> FEATURE:
<223> OTHER INFORMATION: DNA sequence of the 3' UTR, T-ANDge.Hsp/Sb.Hsp,
      a chimeric 3' UTR derived from heat shock protein genes from
      Andropogon gerardii (big bluestem) and Sorghum bicolor (Sorghum).

<400> SEQUENCE: 5
actcctggtc cgcacgtccg gtcgtcgtgc ctgcgtgatt ggaggaaacg gcagttcgtc        60
tcggtcgttt tgtgaaataa ataaaatcat agagtgtttg tcactaatat ggtggtagtg      120
tggtatgatg gtggaatgtg gtcagaaact ctgcgtctct ttcgtatgta ctccgtccgt      180
atgatgtgag tatatctcgt gagtttgctc tttatctaag aatttcttca tttgtggtat     240
cttaagatct gtgttcatgt ttttcagttt ttgtcgcttt attgtatctc atcatcctaa     300
taagttggta atccattctc tc                                                322

<210> SEQ ID NO 6
<211> LENGTH: 2659
<212> TYPE: DNA
<213> ORGANISM: Artificial
<220> FEATURE:
<223> OTHER INFORMATION: DNA sequence of an EXP, EXP-Zm.LTP-SETit.Act4
      comprising a promoter and 5' UTR derived from a lipid transfer
      protein-like protein gene from Zea mays, operably linked 5' to an
      intron derived from an actin 4 gene from Setaria italica.

<400> SEQUENCE: 6
tgttcggatt catccctctc ttagatgccc acgttccttc tagagagcat ttgatcctgc        60
ttgcacggat gaaggggggag cgacacactt acatgggtgc tctaacaagg atcaatgagg      120
agtgttgact ctctgatatc tcgataaaac atcatcatat taataatcct tctttacttt     180
```

```
gaacatttac attcaagcaa ttcaattctt gttttgtatt actataattg tcatgctgaa    240
atatggttga aacgcagtag gacgtagaaa ttttatgata taattgaaaa tttatgtatg    300
cttaaagagt gaagtgggct attcgatagc attgatctat tataagaagt attattttaa    360
tataatttac cgttcttttg gacatcttag tcttgtatta aactatttttt gaacttatgc   420 acgtcattta tgtttcttaa gcttggagct tgccaagtgt tttctggact ttgtgaagtg    480
catgaagcac tcggcaaaag agttatctgc ggtagtgaag agttcgggta aatttattag    540
tacactcttt tttcataaac aagcggaacc atctagccaa cagtacgtca tacaaaaagg    600
gcacccaccg ttgtttgtgg gaatgctttt taagcaaatt caagcctcta actttgaatg    660
ttccaactga acataataaa ccttgacccg atcaggaaca gagctaaagc aaattttagt    720
gattgcaatt gccttctgag cgcattcagt tttaccatgc aagggtgcac ccgtacccac    780
cgctatatgc aattatgcat agctctgcgc ttggatcccg tgaagtgcag aaaaaaaaat    840
acttcaactg ttcaacaact tgggcgtcca ccgtccatgc atcaccatga tacctctgct    900
gatgtttagc actcgatcac gttactagat acaagcagcc aacccatatg acaagttcgt    960
cctaaactga ataaaaatga tcaaccatca agcgagaaca acatcaaca tgcatccacc    1020 agtggagcaa tcttggccac ttgcgctgtt ctgcattgat cagccatcta attaataatc    1080
gccctcacat gcactcatgc tcacgggaat gtaaactcac acaacaacac tgctattaca    1140
ataatcggca ctgcgccgat ggttctccta taaatgcaac aatcaagcgc caccacgaac    1200
catcacaagc gcttagtgat cagttaatac taagggcagg cacacctctg cttcgcgcta    1260
gtgatcaagc aagtgctttc tgtactctgc agcatccccg gtaatctcct cctccccctc    1320
ccctccgctc cctggagccc ctctactcgc gatctcccca cgcactagct cctgctccag    1380 cattttttcga gtgtttggcg ctcagatctg agcggcctgg ctcgagatct gcggtttgct    1440
catgcgttct ggtcacttgc ctccggtgct cccgccagat ccggggcggg taccgcgcga    1500
tccgccagcg gatcgtgctt cgtggttggt gctagggtgt tcgtctgacg tctgtgcttg    1560
atgaactccg tcctgttcct gatctgtagc gtttctgcgt gccgatgcgt ctgattttgt    1620
gcgcacgcct gatgtgtgtt tgcgggactg ccgtgcgagg aggctctctg agctacgtac    1680
ctaggaatgg tgactgtgat gtgcctgaat gcgcttacgt gttgctggcg atgcacgagc    1740
ccttggggtg tgactgcttg actacttccc agctccgacg ttctagtttc ctgcttgact    1800
gggagtctgg gagagcttcg tgatgctctg tctagcaagt ccagatagtt gcggtaactg    1860
gtaacatggt tggatgaaag tcgcggatag ttaatttggt gtgattgaac taccagagtg    1920
taaaaatccg tgtgtggttc attcggagag agctatttgg aaagcatatc tgcatgttag    1980
gatgtttcct tgtcatgaat agctattgag cacataccac ccaaaattag tgacaactta    2040
gtgatgtttc atggcaccaa atgttaggct gaaaagttca gcatgtgatt tttgttgctc    2100
tgcaggtcac atttagaca acaaaaaagc ttgttagatt ggccagtaca tgtacactac    2160 ttttttcaaag caatgctagt cttttcctat catgtttagt tatacgaatg tttggttatg    2220
gtactttaca cattttttata aatgttggaa acaacagtcc gcaagttatc agattatttc    2280
ttactctctc cgttccaaat tgtaggtcgt tttgactttt gtaggttcat agatatattt    2340
atgcatctag atatagtgta tgtctaggtg cataataata tctatgaatc tagaaaagtc    2400
aaaacgacct acaatttgga acggagggag tacaacatta gcctagtcgg tgaaatgaat    2460
cccacttttg cctggcagta agctctgtac atatgttgtt tttattgact tatagatgca    2520
```

```
caaatataaa ggttcagttg atatgccttc aaaacttta tgtttacgat gcttactggt   2580
tcccttgtac agctactatc tagcaggata cacttgctgt taactgatac ccctttttg    2640 ctacctcttg cagggtagc                                                2659
```

<210> SEQ ID NO 7
<211> LENGTH: 1201
<212> TYPE: DNA
<213> ORGANISM: Zea mays
<220> FEATURE:
<221> NAME/KEY: misc_feature
<222> LOCATION: (1)..(1201)
<223> OTHER INFORMATION: DNA sequence of a promoter, P-Zm.Ltp-1:1:2,
      derived from a lipid transfer protein-like protein from Zea mays.

<400> SEQUENCE: 7

```
tgttcggatt catccctctc ttagatgccc acgttccttc tagagagcat ttgatcctgc   60
ttgcacggat gaaggggag cgacacactt acatgggtgc tctaacaagg atcaatgagg    120
agtgttgact ctctgatatc tcgataaaac atcatcatat taataatcct tctttacttt   180
gaacatttac attcaagcaa ttcaattctt gttttgtatt actataattg tcatgctgaa   240
atatggttga aacgcagtag gacgtagaaa ttttatgata taattgaaaa tttatgtatg   300
cttaaagagt gaagtgggct attcgatagc attgatctat tataagaagt attattttaa   360
tataatttac cgttcttttg gacatcttag tcttgtatta aactattttt gaacttatgc   420
acgtcattta tgtttcttaa gcttggagct tgccaagtgt tttctggact ttgtgaagtg   480
catgaagcac tcggcaaaag agttatctgc ggtagtgaag agttcgggta aatttattag   540
tacactcttt tttcataaac aagcggaacc atctagccaa cagtacgtca tacaaaaagg   600
gcacccaccg ttgtttgtgg gaatgctttt taagcaaatt caagcctcta actttgaatg   660
ttccaactga acataataaa ccttgacccg atcaggaaca gagctaaagc aaattttagt   720
gattgcaatt gccttctgag cgcattcagt tttaccatgc aagggtgcac ccgtacccac   780
cgctatatgc aattatgcat agctctgcgc ttggatcccg tgaagtgcag aaaaaaaaat   840
acttcaactg ttcaacaact tgggcgtcca ccgtccatgc atcaccatga tacctctgct   900
gatgtttagc actcgatcac gttactagat acaagcagcc aacccatatg acaagttcgt   960
cctaaactga ataaaaatga tcaaccatca agcgagaaca aacatcaaca tgcatccacc   1020
agtggagcaa tcttggccac ttgcgctgtt ctgcattgat cagccatcta attaataatc   1080
gccctcacat gcactcatgc tcacgggaat gtaaactcac acaacaacac tgctattaca   1140
ataatcggca ctgcgccgat ggttctccta taaatgcaac aatcaagcgc caccacgaac   1200
c                                                                   1201
```

<210> SEQ ID NO 8
<211> LENGTH: 93
<212> TYPE: DNA
<213> ORGANISM: Zea mays
<220> FEATURE:
<221> NAME/KEY: misc_feature
<222> LOCATION: (1)..(93)
<223> OTHER INFORMATION: DNA sequence of a 5' UTR, L-Zm.Ltp-1:1:3,
      derived from a lipid transfer protein-like protein from Zea mays.

<400> SEQUENCE: 8

```
atcacaagcg cttagtgatc agttaatact aagggcaggc acacctctgc ttcgcgctag   60
tgatcaagca agtgctttct gtactctgca gca                                93
```

<210> SEQ ID NO 9
<211> LENGTH: 1365
<212> TYPE: DNA
<213> ORGANISM: Setaria italica
<220> FEATURE:
<221> NAME/KEY: misc_feature
<222> LOCATION: (1)..(1365)
<223> OTHER INFORMATION: DNA sequence of an intron, I-SETit.Act4:2, derived from an actin 4 gene from Setaria italica.

<400> SEQUENCE: 9

```
tccccggtaa tctcctcctc ccctcccct ccgctccctg gagcccctct actcgcgatc      60
tccccacgca ctagctcctg ctccagcatt tttcgagtgt ttggcgctca gatctgagcg    120
gcctggctcg agatctgcgg tttgctcatg cgttctggtc acttgcctcc ggtgctcccg    180
ccagatccgg ggcgggtacc gcgcgatccg ccagcggatc gtgcttcgtg gttggtgcta    240
gggtgttcgt ctgacgtctg tgcttgatga actccgtcct gttcctgatc tgtagcgttt    300
ctgcgtgccg atgcgtctga ttttgtgcgc acgcctgatg tgtgtttgcg ggactgccgt    360
gcgaggaggc tctctgagct acgtacctag gaatggtgac tgtgatgtgc ctgaatgcgc    420
ttacgtgttg ctggcgatgc acgagcccct ggggtgtgac tgcttgacta cttcccagct    480
ccgacgttct agtttcctgc ttgactggga gtctgggaga gcttcgtgat gctctgtcta    540
gcaagtccag atagttgcgg taactggtaa catggttgga tgaaagtcgc ggatagttaa    600
tttggtgtga ttgaactacc agagtgtaaa atccgtgtg tggttcattc ggagagagct     660
atttggaaag catatctgca tgttaggatg tttccttgtc atgaatagct attgagcaca    720
taccacccaa aattagtgac aacttagtga tgtttcatgg caccaaatgt taggctgaaa    780
agttcagcat gtgattttg ttgctctgca ggtcacattt tagacaacaa aaaagcttgt     840
tagattggcc agtacatgta cactactttt tcaaagcaat gctagtcttt tcctatcatg    900
tttagttata cgaatgtttg gttatggtac tttacacatt tttataaatg ttggaaacaa    960
cagtccgcaa gttatcagat tatttcttac tctctccgtt ccaaattgta ggtcgttttg   1020
acttttgtag gttcatagat attattatgc atctagatat agtgtatgtc taggtgcata   1080
ataatatcta tgaatctaga aaagtcaaaa cgacctacaa tttggaacgg agggagtaca   1140
acattagcct agtcggtgaa atgaatccca cttttgcctg gcagtaagct ctgtacatat   1200
gttgttttta ttgacttata gatgcacaaa tataaaggtt cagttgatat gccttcaaaa   1260
cttttatgtt tacgatgctt actggttccc ttgtacagct actatctagc aggatacact   1320
tgctgttaac tgatacccct ttttgctac ctcttgcagg gtagc                    1365
```

<210> SEQ ID NO 10
<211> LENGTH: 477
<212> TYPE: DNA
<213> ORGANISM: Cauliflower mosaic virus
<220> FEATURE:
<221> NAME/KEY: misc_feature
<222> LOCATION: (1)..(477)
<223> OTHER INFORMATION: DNA sequence of an enhancer, E-CaMV.35S-RC derived from the Cauliflower mosaic virus 35S promoter in a reverse compliment orientation.

<400> SEQUENCE: 10

```
aggatagtgg gattgtgcgt catcccttac gtcagtggag atatcacatc aatccacttg     60
ctttgaagac gtggttggaa cgtcttcttt ttccacgatg ctcctcgtgg gtggggtcc    120 atctttggga ccactgtcgg cagaggcatc ttgaacgata gcctttcctt tatcgcaatg    180
atggactttg taggagccac cttccttttc tactgtcctt tccatgaagt gacagataga    240
```

```
tgggcaatgg aatccgagga ggtttcctga tattacccct tgttgaaaag tctcaatagc    300
cctttggtct tctgagactg tatctttgat attcttggag tagacgagag tgtcgtgctc    360
caccatgttg acgaagattt tcttcttgtc attgagtcgt aaaagactct gtatgaactg    420
tccgccagtc ttcacggcga gttctgttag atcctcgatc tgaattttg actcctt       477

<210> SEQ ID NO 11
<211> LENGTH: 2001
<212> TYPE: DNA
<213> ORGANISM: Artificial
<220> FEATURE:
<223> OTHER INFORMATION: Synthetic coding sequence optimized for plant
      expression for beta-glucuronidase (GUS) with a processable intron
      derived from the potato light-inducible tissue-specific ST-LS1
      gene (GenBank Accession: X04753).

<400> SEQUENCE: 11
atggtgaggc ccgttgagac cccgactagg gagatcaaga agctggacgg cctctgggcc    60
ttctccctcg accgtgagaa ctgcggcatc gaccagcgct ggtgggagtc cgccctccag   120
gagtctaggg ccatcgccgt gcccggttcc ttcaacgacc agttcgccga cgccgacatc   180
cgcaactacg cgggcaacgt ctggtatcag cgcgaggtgt catcccgaa gggctgggcg    240 ggccagcgca tcgtgctccg cttcgacgcc gtgacccact acggcaaggt ctgggtgaac   300
aatcaggagg taagtttctg cttctacctt tgatatatat ataataatta tcattaatta   360
gtagtaatat aatatttcaa atattttttt caaaataaaa gaatgtagta tatagcaatt   420
gcttttctgt agtttataag tgtgtatatt ttaatttata acttttctaa tatatgacca   480
aaatttgttg atgtgcaggt gatggagcac cagggcggtt acaccccgtt cgaggccgac   540
gtgacgccgt acgtgatcgc cgggaagtcc gtccgcatca ccgtctgcgt gaacaatgag   600
ctgaactggc agaccatccc gcctggcatg gtcatcaccg acgagaacgg caagaagaag   660
cagtcctact ccacgacttc ttcaactac gctggcatcc accgctccgt gatgctctac   720
accactccca cacctgggt ggacgacatc accgtggtca cccacgtggc ccaggactgc   780
aaccacgcct ccgtggactg gcaagtcgtt gccaacggcg acgtcagcgt cgagctgcgc   840
gacgccgacc agcaagtcgt tgccaccggc cagggcacca gcggcacccct ccaagtcgtc   900 aaccctcacc tctggcagcc tggcgaggggc tacctctacg agctgtgcgt caccgccaag   960
agccagactg agtgcgacat ctaccctctc cgcgtcggca tcaggagcgt cgctgtcaag  1020
ggcgagcagt tcctcatcaa ccacaagcct ttctacttca ctggtttcgg ccgccacgag  1080
gacgctgacc tgaggggcaa gggtttcgac aacgtcctga tggtccacga ccacgctctg  1140
atggactgga tcggtgccaa cagctacagg accagtcact acccgtacgc tgaggagatg  1200
ctggactggg ctgacgagca cggtatcgtc gtgatcgacg agactgctgc ggtcggtttc  1260
aacctgtctc tgggcattgg tttcgaggct gggaacaagc gaaggagct gtactctgag  1320 gaagctgtca acgcgagac tcagcaagct catctccagg cgattaagga gctgattgcc  1380
agggacaaga accatccgtc tgtcgtgatg tggtctattg cgaatgagcc ggacaccaga  1440
ccgcaagggg cgcgtgaata cttcgcgccg ctggcggagg cgactcgcaa actgaccca  1500 acccgtccaa tcacgtgcgt caatgtcatg ttctgcgacg cccatacgga tacgatctcg  1560
gacctgttcg atgttctttg tctcaatcgg tactatgggt ggtatgttca gagcggggat  1620
cttgagacgc ggagaaggt tcttgagaag gaactcctgg cgtggcaaga gaagctccat  1680
cagccgatca ttatcacgga gtacgggttt gacacacttg cgggccttca cagtatgtac  1740
```

```
acagatatgt ggtcggagga ataccagtgt gcatggttgg atatgtacca tcgtgtcttc   1800
gaccgggttt cagcggttgt cggcgaacaa gtctggaact tcgcagactt cgccacgagc   1860
caagggatac tgcgggtagg agggaacaag aagggaatct tcacacggga tcggaagccc   1920
aagtcagcag ccttcctgtt gcagaagcga tggacaggaa tgaacttcgg agaaaagcca   1980
cagcaaggcg aaagcagtg a                                               2001
```

```
<210> SEQ ID NO 12
<211> LENGTH: 572
<212> TYPE: DNA
<213> ORGANISM: Saccharum ravennae
<220> FEATURE:
<221> NAME/KEY: misc_feature
<222> LOCATION: (1)..(572)
<223> OTHER INFORMATION: DNA sequence of a 3' UTR, T-Cl.Hsp16.9:2,
      derived from the Hsp16.9 (Heat shock protein 16.9) protein gene
      from Saccharum ravennae (hardy pampas grass).

<400> SEQUENCE: 12
gcgaccatgg acgttggatg atgaagatgt ggcaacggtg tggagtgtga tatcctgttt    60
tgtttcccgg tcgtgattgt ttgctgtgtc agatggttta ctgcagcttc atgtgaagtc   120
tactgcctgc tacagtgcta ctccttggac ttttgagtaa tctgcaatca gtattctcca   180
tgtgtaatcg tctttgagat tatataaaag taaataaagc atcttctcca cctttccgga   240
aaaccatgag atcatcctac tcctatagtt tttaatactc cgttcgttct aatttctaaa   300
aaaatgtaaa ctcacttctc caggagtgaa ttaactttaa ctaaaccgaa aaaacaatag   360
ttatgatgcg taataagtct tattagatca atcatgaact atatttttat aatgaaccta   420
tttagagata aaaacttaat gtagaagtga gattcatatt cttttaaaac agagagagta   480
catgcgttta acagtgtgcg agtgaaaatt ttactcattc ctcctctatt ttggtgcagg   540
gcacaacgtg gtacttgtac gtgcccctgg ta                                 572
```

```
<210> SEQ ID NO 13
<211> LENGTH: 572
<212> TYPE: DNA
<213> ORGANISM: Coix lacryma-jobi
<220> FEATURE:
<221> NAME/KEY: misc_feature
<222> LOCATION: (1)..(572)
<223> OTHER INFORMATION: DNA sequence of a 3' UTR, T-Cl.Hsp16.9:2,
      derived from the Hsp16.9 (heat shock protein 16.9) protein gene
      from Coix lacryma-jobi (Job's tears).

<400> SEQUENCE: 13
aggagcctgg gcgctttata tatgctcaaa ataccgatgc tgccgtcttc gtctgtgtcg    60
atcgatcggg tagttcttcg catgtcgggt ccataaaaat gctcgcgtcc gtgtaataca   120
cttgtcactg tgctggtatc atggatgatt ggatggctgt cttgagtagc gtgtgtcgtg   180
gctgctgtgt ttcgaacgag attaaagtgt cgtgcgttgt gtattgtgtc gcctgttgcg   240
tgatcgcgtc tgtaataaac ccagtttcaa agaatttcca agtgacttgc tagtttctag   300
tgttctacgg cttctttgga ataaattcct aaggtactcg taataagctt acaattaaca   360
tgttcgatca ctatcatgac aaagtagctt ccatttcctt acagttcaga tgtctcatcg   420
aacacgttgg atctacagaa ataccgttc gttttttttcc cccagttctt gtggagaccc   480
cacaaccagt atctaaggat cgacatataa acacacagta gtctactggt atgttctctc   540
ttattaaatc agcatatagc caacttgtag ca                                 572
```

<210> SEQ ID NO 14
<211> LENGTH: 496
<212> TYPE: DNA
<213> ORGANISM: Artificial
<220> FEATURE:
<223> OTHER INFORMATION: DNA sequence of a chimeric-rearranged enhancer,
      E-DaMV.H-Flt:1, derived from multiple public Dahlia mosaic virus
      promoters.

<400> SEQUENCE: 14
taactgggat ttttggagga ttctgatgaa accatttacc ctaacttgag ataactggag 60
taaaagatcc ttactgtcca ccatttcttg tgatgggtta aaatccctct tgccggagag 120
acctatctct atcaggtgat atgcctggta gctgtttcct tcttcccaat ctggcaggcc 180
cttgttcgtc actgctgacg tctttttcct cattattgga ggatgagtca ctgcaagctg 240
taaagcttgt attattgctg gtggaggccc caccttcaca tgctgagcat ttatggttgt 300
cggccaataa tttcttcagc tgtttgcaaa gcaataattt tgtagatgtc cctacatcaa 360
ctttggcatg tgcaatgctt tcttcaaagg aagataagat gtcaacatct tgtctggaga 420
ttggtgctcc gtagtgactc atgatcaata ccttttctg tgcgtaattg atcttgattt 480
ttgtcttccc gtcgat 496

<210> SEQ ID NO 15
<211> LENGTH: 322
<212> TYPE: DNA
<213> ORGANISM: Dahlia mosaic virus
<220> FEATURE:
<221> NAME/KEY: misc_feature
<222> LOCATION: (1)..(322)
<223> OTHER INFORMATION: DNA sequence of an enhancer, E-DaMV.FLT:2, derived from a Dalia mosaic virus promoter, Genbank accession EF513491, nucleotides 1 through 322.

<400> SEQUENCE: 15
atcaacggag aaacaaagat aaaaatcaat tactcacatg aaagagtatt gatcacgagt 60
cactatggag cgacaatctc cagacaggat gtcagcatct tatcttcctt tgaagaaagc 120
atcatcaata acgatgtaat ggtggggaca tccactaagt tattgctctg caaacagctc 180
aaaaagctac tggccgacaa tcataattgc tcggcatgtg caggtggggc ctccactagc 240
aataatacaa gctttacagc ttgcagtgac tcatcctcca ataatggaga aaaagacgtc 300
agcagtgacg aacaagggtc ga 322

<210> SEQ ID NO 16
<211> LENGTH: 3163
<212> TYPE: DNA
<213> ORGANISM: Artificial
<220> FEATURE:
<223> OTHER INFORMATION: DNA sequence of an EXP, EXP-DaMV.H-Flt+Zm.Ltp+SETit.Act4:1 comprised of the chimeric-rearranged enhancer, E-DaMV.H-Flt:1, operably linked 5' to the EXP, EXP-Zm.LTP-SETit.Act4.

<400> SEQUENCE: 16
atcgacggga agacaaaaat caagatcaat tacgcacaga aaaaggtatt gatcatgagt 60
cactacggag caccaatctc cagacaagat gttgacatct tatcttcctt tgaagaaagc 120
attgcacatg ccaaagttga tgtagggaca tctacaaaat tattgctttg caaacagctg 180
aagaaattat tggccgacaa ccataaatgc tcagcatgtg aaggtggggc ctccaccagc 240
aataatacaa gctttacagc ttgcagtgac tcatcctcca ataatgagga aaaagacgtc 300

```
agcagtgacg aacaagggcc tgccagattg ggaagaagga acagctacc  aggcatatca    360 cctgatagag ataggtctct ccggcaagag ggattttaac ccatcacaag aaatggtgga    420
cagtaaggat cttttactcc agttatctca agttagggta aatggtttca tcagaatcct    480
ccaaaaatcc cagttatgtt cggattcatc cctctcttag atgcccacgt tccttctaga    540
gagcatttga tcctgcttgc acggatgaag ggggagcgac acacttacat gggtgctcta    600
acaaggatca atgaggagtg ttgactctct gatatctcga taaacatca  tcatattaat    660 aatccttctt tactttgaac atttacattc aagcaattca attcttgttt tgtattacta    720
taattgtcat gctgaaatat ggttgaaacg cagtaggacg tagaaatttt atgatataat    780
tgaaaattta tgtatgctta agagtgaag  tgggctattc gatagcattg atctattata    840
agaagtatta ttttaatata atttaccgtt cttttggaca tcttagtctt gtattaaact    900
atttttgaac ttatgcacgt catttatgtt tcttaagctt ggagcttgcc aagtgttttc    960
tggactttgt gaagtgcatg aagcactcgg caaagagtt  atctgcggta gtgaagagtt   1020
cgggtaaatt tattagtaca ctcttttttc ataaacaagc ggaaccatct agccaacagt   1080
acgtcataca aaaagggcac ccaccgttgt ttgtgggaat gcttttaag  caaattcaag   1140 cctctaactt tgaatgttcc aactgaacat aataaacctt gacccgatca ggaacagagc   1200
taaagcaaat tttagtgatt gcaattgcct tctgagcgca ttcagtttta ccatgcaagg   1260
gtgcacccgt acccaccgct atatgcaatt atgcatagct ctgcgcttgg atcccgtgaa   1320
gtgcagaaaa aaaatactt  caactgttca acaacttggg cgtccaccgt ccatgcatca   1380
ccatgatacc tctgctgatg tttagcactc gatcacgtta ctagatacaa gcagccaacc   1440
catatgacaa gttcgtccta aactgaataa aaatgatcaa ccatcaagcg agaacaaaca   1500
tcaacatgca tccaccagtg gagcaatctt ggccacttgc gctgttctgc attgatcagc   1560
catctaatta ataatcgccc tcacatgcac tcatgctcac gggaatgtaa actcacacaa   1620
caacactgct attacaataa tcggcactgc gccgatggtt ctcctataaa tgcaacaatc   1680
aagcgccacc acgaaccatc acaagcgctt agtgatcagt taatactaag ggcaggcaca   1740
cctctgcttc gcgctagtga tcaagcaagt gcttctgta  ctctgcagca ggccggcctc   1800
cccggtaatc tcctcctccc cctcccctcc gctccctgga gcccctctac tcgcgatctc   1860
cccacgcact agctcctgct ccagcatttt tcgagtgttt ggcgctcaga tctgagcggc   1920
ctggctcgag atctgcggtt tgctcatgcg ttctggtcac ttgcctccgg tgctcccgcc   1980
agatccgggg cgggtaccgc gcgatccgcc agcggatcgt gcttcgtggt tggtgctagg   2040
gtgttcgtct gacgtctgtg cttgatgaac tccgtcctgt tcctgatctg tagcgtttct   2100
gcgtgccgat gcgtctgatt tgtgcgcac  gcctgatgtg tgtttgcggg actgccgtgc   2160
gaggaggctc tctgagctac gtacctagga atggtgactg tgatgtgcct gaatgcgctt   2220
acgtgttgct ggcgatgcac gagcccttgg ggtgtgactg cttgactact tcccagctcc   2280
gacgttctag tttcctgctt gactgggagt ctggagagc  ttcgtgatgc tctgtctagc   2340
aagtccagat agttgcggta actggtaaca tggttggatg aaagtcgcgg atagttaatt   2400
tggtgtgatt gaactaccag agtgtaaaaa tccgtgtgtg gttcattcgg agagagctat   2460
ttggaaagca tatctgcatg ttaggatgtt tccttgtcat gaatagctat tgagcacata   2520
ccacccaaaa ttagtgacaa cttagtgatg tttcatggca ccaaatgtta ggctgaaaag   2580
ttcagcatgt gattttttgtt gctctgcagg tcacatttta gacaacaaaa aagcttgtta   2640
gattggccag tacatgtaca ctactttttc aaagcaatgc tagtcttttc ctatcatgtt   2700
```

```
tagttatacg aatgtttggt tatggtactt tacacatttt tataaatgtt ggaaacaaca    2760
gtccgcaagt tatcagatta tttcttactc tctccgttcc aaattgtagg tcgttttgac    2820
ttttgtaggt tcatagatat tattatgcat ctagatatag tgtatgtcta ggtgcataat    2880
aatatctatg aatctagaaa agtcaaaacg acctacaatt tggaacggag ggagtacaac    2940
attagcctag tcggtgaaat gaatcccact tttgcctggc agtaagctct gtacatatgt    3000 tgttttatt gacttataga tgcacaaata taaaggttca gttgatatgc cttcaaaact    3060
tttatgttta cgatgcttac tggttcccctt gtacagctac tatctagcag gatacacttg    3120
ctgttaactg atacccctttt tttgctacct cttgcagggg agc                    3163
```

<210> SEQ ID NO 17
<211> LENGTH: 3163
<212> TYPE: DNA
<213> ORGANISM: Artificial
<220> FEATURE:
<223> OTHER INFORMATION: DNA sequence of an EXP,
       EXP-DaMV.H-Flt+Zm.Ltp+SETit.Act4:1 comprised of the chimeric-
       rearranged enhancer, E-DaMV.H-Flt:1, operably linked 5' to the
       EXP, EXP-Zm.LTP-SETit.Act4.

<400> SEQUENCE: 17

```
taactgggat ttttggagga ttctgatgaa accatttacc ctaacttgag ataactggag      60
taaaagatcc ttactgtcca ccatttcttg tgatgggtta aaatccctct tgccggagag     120
acctatctct atcaggtgat atgcctggta gctgtttcct tcttcccaat ctggcaggcc     180
cttgttcgtc actgctgacg tctttttcct cattattgga ggatgagtca ctgcaagctg     240
taaagcttgt attattgctg gtggaggccc caccttcaca tgctgagcat ttatggttgt     300
cggccaataa tttcttcagc tgtttgcaaa gcaataattt tgtagatgtc cctacatcaa     360
ctttggcatg tgcaatgctt tcttcaaagg aagataagat gtcaacatct tgtctggaga     420
ttggtgctcc gtagtgactc atgatcaata cctttttctg tgcgtaattg atcttgattt     480
ttgtcttccc gtcgattgtt cggattcatc cctctcttag atgcccacgt tccttctaga     540
gagcatttga tcctgcttgc acggatgaag ggggagcgac acacttacat gggtgctcta     600
acaaggatca atgaggagtg ttgactctct gatatctcga taaaacatca tcatattaat     660
aatccttctt tactttgaac atttacattc aagcaattca attcttgttt tgtattacta     720
taattgtcat gctgaaatat ggttgaaacg cagtaggacg tagaaatttt atgatataat     780
tgaaaattta tgtatgctta aagagtgaag tgggctattc gatagcattg atctattata     840
agaagtatta ttttaatata atttaccgtt cttttggaca tcttagtctt gtattaaact     900
atttttgaac ttatgcacgt catttatgtt tcttaagctt ggagcttgcc aagtgttttc     960
tggactttgt gaagtgcatg aagcactcgg caaaagagtt atctgcggta gtgaagagtt    1020
cgggtaaatt tattagtaca ctcttttttc ataaacaagc ggaaccatct agccaacagt    1080
acgtcataca aaagggcac ccaccgttgt ttgtgggaat gcttttaag caaattcaag    1140 cctctaactt tgaatgttcc aactgaacat aataaacctt gacccgatca ggaacagagc    1200
taaagcaaat tttagtgatt gcaattgcct tctgagcgca ttcagttta ccatgcaagg    1260 gtgcacccgt acccaccgct atatgcaatt atgcatagct ctgcgcttgg atcccgtgaa    1320
gtgcagaaaa aaaatactt caactgttca acaacttggg cgtccaccgt ccatgcatca    1380
ccatgatacc tctgctgatg tttagcactc gatcacgtta ctagatacaa gcagccaacc    1440
catatgacaa gttcgtccta aactgaataa aaatgatcaa ccatcaagcg agaacaaaca    1500
```

```
tcaacatgca tccaccagtg gagcaatctt ggccacttgc gctgttctgc attgatcagc    1560
catctaatta ataatcgccc tcacatgcac tcatgctcac gggaatgtaa actcacacaa    1620
caacactgct attacaataa tcggcactgc gccgatggtt ctcctataaa tgcaacaatc    1680
aagcgccacc acgaaccatc acaagcgctt agtgatcagt taatactaag ggcaggcaca    1740
cctctgcttc gcgctagtga tcaagcaagt gctttctgta ctctgcagca ggccggcctc    1800
cccggtaatc tcctcctccc cctccccctcc gctccctgga gccctctac tcgcgatctc    1860 cccacgcact agctcctgct ccagcatttt tcgagtgttt ggcgctcaga tctgagcggc    1920
ctggctcgag atctgcggtt tgctcatgcg ttctggtcac ttgcctccgg tgctcccgcc    1980
agatccgggg cgggtaccgc gcgatccgcc agcggatcgt gcttcgtggt tggtgctagg    2040
gtgttcgtct gacgtctgtg cttgatgaac tccgtcctgt tcctgatctg tagcgtttct    2100
gcgtgccgat gcgtctgatt ttgtgcgcac gcctgatgtg tgtttgcggg actgccgtgc    2160
gaggaggctc tctgagctac gtacctagga atggtgactg tgatgtgcct gaatgcgctt    2220
acgtgttgct ggcgatgcac gagcccttgg ggtgtgactg cttgactact tcccagctcc    2280
gacgttctag tttcctgctt gactgggagt ctggagagc ttcgtgatgc tctgtctagc    2340
aagtccagat agttgcggta actggtaaca tggttggatg aaagtcgcgg atagttaatt    2400
tggtgtgatt gaactaccag agtgtaaaaa tccgtgtgtg gttcattcgg agagagctat    2460
ttggaaagca tatctgcatg ttaggatgtt tccttgtcat gaatagctat tgagcacata    2520
ccacccaaaa ttagtgacaa cttagtgatg tttcatggca ccaaatgtta ggctgaaaag    2580
ttcagcatgt gatttttgtt gctctgcagg tcacatttta gacaacaaaa aagcttgtta    2640
gattggccag tacatgtaca ctactttttc aaagcaatgc tagtcttttc ctatcatgtt    2700
tagttatacg aatgtttggt tatggtactt tacacatttt tataaatgtt ggaaacaaca    2760
gtccgcaagt tatcagatta tttcttactc tctccgttcc aaattgtagg tcgttttgac    2820
ttttgtaggt tcatagatat tattatgcat ctagatatag tgtatgtcta ggtgcataat    2880
aatatctatg aatctagaaa agtcaaaacg acctacaatt tggaacggag ggagtacaac    2940
attagcctag tcggtgaaat gaatcccact tttgcctggc agtaagctct gtacatatgt    3000 tgttttatt gacttataga tgcacaaata taaaggttca gttgatatgc cttcaaaact    3060
tttatgttta cgatgcttac tggttcccctt gtacagctac tatctagcag gatacacttg    3120
ctgttaactg atacccctttt tttgctacct cttgcagggt agc                     3163
```

<210> SEQ ID NO 18
<211> LENGTH: 1271
<212> TYPE: DNA
<213> ORGANISM: Artificial
<220> FEATURE:
<223> OTHER INFORMATION: DNA sequence of an EXP,
    EXP-DaMV.FLT+Td.RCc3_1+SETit.14-3-3C-5:1 comprised of the
    enhancer, E-DaMV.FLT:2 operably linked 5' to a promoter, leader,
    and intron.

<400> SEQUENCE: 18

```
tcgacccttg ttcgtcactg ctgacgtctt tttctccatt attggaggat gagtcactgc      60
aagctgtaaa gcttgtatta ttgctagtgg aggccccacc tgcacatgcc gagcaattat     120
gattgtcggc cagtagcttt tgagctgtt tgcagagcaa taacttagtg gatgtcccca     180
ccattacatc gttattgatg atgctttctt caaaggaaga taagatgctg acatcctgtc     240
tggagattgt cgctccatag tgactcgtga tcaatactct ttcatgtgag taattgattt     300
```

```
ttatctttgt ttctccgttg atggcctact aggccaaatg gatgaaacaa cttggaccaa      360
tcagagatgg ccacgtcagc tcccgatcgt cgtaaccgac caaacccgat cgataacggt      420
ttaggctcca atacaccgtc ggtaccaccc ggtcgctatc atctgccccc gtcccaacgc      480
tattggtatc gtccgcccct atatcggtcg gtagcccagt ccaccgtcgg ggccaatcgt      540
cccctgctgc gtccgctcgt gtcggtaccg atcgccaaaa acgccacgtc aacggcactg      600
cggtaccgac cgccgctggc accggcctta gcgggccaca cgaccgatcg ctgttgtacg      660
gacgtagagg tgaatcatgc gattgaattt cgctagagg aaagttatca tcttattatc       720
tccaaccctc cttcctacgg ctggatccga cgaaaattta ccctggacgg tgccagtaac      780
aattgcaggt ctcactcacg tgctaaatcc agcaatcaaa cacgaaggaa tatacgtgat      840
ctggccagaa catgcaagag aataatacag tagtgttaga gtacgaaacc tacacgattc      900
aacgaattaa tcaatgggtt cacgttcacg ggtatgctcg cgcacgtcca aaatccaacg      960
acatttttat aagcggcatg atccagacgg gccagctcga gcaccacatg gcgtggctcc     1020
atctcgcatc ccccatcacc gctataaata ccattggcca tgcacacccg cactcccaca     1080
cagcacaagc agcagcagca gcagcagctc gatcgaacta gcttagctac tacgtgcgcg     1140
tgcaacaagc agctcgatcg atcgccctca cggtaatttc ttctcccaaa ataaacctaa     1200
tctttaatct gttgcctgtc tactcttcct atctgttgct aaaaatttga atttggtatg     1260
tgcaggagga c                                                         1271
```

<210> SEQ ID NO 19
<211> LENGTH: 1271
<212> TYPE: DNA
<213> ORGANISM: Artificial
<220> FEATURE:
<223> OTHER INFORMATION: DNA sequence of an EXP,
      EXP-DaMV.FLT+Td.RCc3_1+SETit.14-3-3C-5:1 comprised of the
      enhancer, E-DaMV.FLT:2 operably linked 5' to a promoter, leader, and intron.

<400> SEQUENCE: 19

```
atcaacggag aaacaaagat aaaaatcaat tactcacatg aaagagtatt gatcacgagt     60
cactatggag cgacaatctc cagacaggat gtcagcatct tatcttcctt tgaagaaagc    120
atcatcaata acgatgtaat ggtggggaca tccactaagt tattgctctg caaacagctc    180
aaaaagctac tggccgacaa tcataattgc tcggcatgtg caggtggggc ctccactagc    240
aataatacaa gctttacagc ttgcagtgac tcatcctcca ataatggaga aaaagacgtc    300
agcagtgacg aacaagggtc gaggcctact aggccaaatg gatgaaacaa cttggaccaa    360
tcagagatgg ccacgtcagc tcccgatcgt cgtaaccgac caaacccgat cgataacggt    420
ttaggctcca atacaccgtc ggtaccaccc ggtcgctatc atctgccccc gtcccaacgc    480
tattggtatc gtccgcccct atatcggtcg gtagcccagt ccaccgtcgg ggccaatcgt    540
cccctgctgc gtccgctcgt gtcggtaccg atcgccaaaa acgccacgtc aacggcactg    600
cggtaccgac cgccgctggc accggcctta gcgggccaca cgaccgatcg ctgttgtacg    660
gacgtagagg tgaatcatgc gattgaattt tcgctagagg aaagttatca tcttattatc    720
tccaaccctc cttcctacgg ctggatccga cgaaaattta ccctggacgg tgccagtaac    780
aattgcaggt ctcactcacg tgctaaatcc agcaatcaaa cacgaaggaa tatacgtgat    840
ctggccagaa catgcaagag aataatacag tagtgttaga gtacgaaacc tacacgattc    900
aacgaattaa tcaatgggtt cacgttcacg ggtatgctcg cgcacgtcca aaatccaacg    960
```

-continued

```
acatttttat aagcggcatg atccagacgg gccagctcga gcaccacatg gcgtggctcc    1020
atctcgcatc ccccatcacc gctataaata ccattggcca tgcacacccg cactcccaca    1080
cagcacaagc agcagcagca gcagcagctc gatcgaacta gcttagctac tacgtgcgcg    1140
tgcaacaagc agctcgatcg atcgccctca cggtaatttc ttctcccaaa ataaacctaa    1200
tctttaatct gttgcctgtc tactcttcct atctgttgct aaaaatttga atttggtatg    1260
tgcaggagga c                                                         1271
```